(12) United States Patent
Boal et al.

(10) Patent No.: US 10,493,440 B2
(45) Date of Patent: Dec. 3, 2019

(54) METHODS TO PRODUCE MOLECULAR SIEVES WITH LTA TOPOLOGY AND COMPOSITIONS DERIVED THEREFROM

(71) Applicant: CALIFORNIA INSTITUTE OF TECHNOLOGY, Pasadena, CA (US)

(72) Inventors: Ben W. Boal, Pasadena, CA (US); Mark E. Davis, Pasadena, CA (US); Joel E. Schmidt, Utrecht (NL)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 15/730,003

(22) Filed: Oct. 11, 2017

(65) Prior Publication Data

US 2018/0029021 A1 Feb. 1, 2018

Related U.S. Application Data

(62) Division of application No. 15/063,867, filed on Mar. 8, 2016, now Pat. No. 9,821,297.

(Continued)

(51) Int. Cl.
*B01J 29/70* (2006.01)
*C01B 39/14* (2006.01)
(Continued)

(52) U.S. Cl.
CPC ......... *B01J 29/047* (2013.01); *B01J 29/7003* (2013.01); *B01J 29/7053* (2013.01);
(Continued)

(58) Field of Classification Search
CPC ....... C01B 39/06; C01B 39/14; C01B 39/145; C01B 39/48; B01J 29/7003;
(Continued)

(56) References Cited

U.S. PATENT DOCUMENTS 3,306,922 A * 2/1967 Barrer ................. C01B 33/2876
556/173
4,410,501 A * 10/1983 Taramasso ............... B01J 29/89
423/705

(Continued)

FOREIGN PATENT DOCUMENTS

WO        99/08961 A1    2/1999
WO    2014/210560 A1   12/2014

OTHER PUBLICATIONS

"LTA, International Zeolite Commision", LTA Materails, downloaded Nov. 26, 2018 (Year: 2018).*

(Continued)

*Primary Examiner* — David M Brunsman
(74) *Attorney, Agent, or Firm* — BakerHostetler

(57) ABSTRACT

The present disclosure is directed to processing for preparing crystalline pure-silica and heteroatom-substituted LTA frameworks in fluoride media using a simple organic structure-directing agent (OSDA), having a structure of Formula (I):

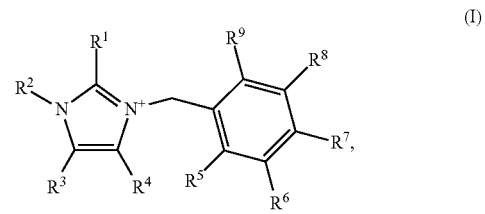

where substituents $R^1$ to $R^9$ are defined herein. Aluminosilicate LTA is an active catalyst for the methanol to olefins reaction with higher product selectivities to butenes as well as C5 and C6 products than the commercialized catalysts.

(Continued)

Titanosilicate LTA is an active catalyst for the epoxidation of allyl alcohol using aqueous $H_2O_2$.

25 Claims, 15 Drawing Sheets

Related U.S. Application Data

(60) Provisional application No. 62/204,876, filed on Aug. 13, 2015, provisional application No. 62/131,116, filed on Mar. 10, 2015.

(51) Int. Cl.

| | | |
|---|---|---|
| *C01B 39/48* | (2006.01) | |
| *B01J 29/04* | (2006.01) | |
| *C01B 37/00* | (2006.01) | |
| *C07C 1/20* | (2006.01) | |
| *C07D 301/12* | (2006.01) | |
| *B01J 29/78* | (2006.01) | |
| *B01J 29/74* | (2006.01) | |
| *B01J 29/89* | (2006.01) | |
| *B01J 35/00* | (2006.01) | |
| *B01J 35/02* | (2006.01) | |
| *C01B 37/02* | (2006.01) | |
| *B01J 29/85* | (2006.01) | |
| *B01D 53/94* | (2006.01) | |

(52) U.S. Cl.
CPC ....... *B01J 29/7407* (2013.01); *B01J 29/7807* (2013.01); *B01J 29/89* (2013.01); *B01J 35/002* (2013.01); *B01J 35/023* (2013.01); *C01B 37/005* (2013.01); *C01B 37/02* (2013.01); *C01B 39/145* (2013.01); *C07C 1/20* (2013.01); *C07D 301/12* (2013.01); *B01D 53/9413* (2013.01); *B01D 2255/20707* (2013.01); *B01D 2255/50* (2013.01); *B01J 29/70* (2013.01); *B01J 29/7007* (2013.01); *B01J 29/7015* (2013.01); *B01J 29/85* (2013.01); *C07C 2523/08* (2013.01); *C07C 2529/70* (2013.01); *C07C 2529/89* (2013.01); *Y02P 20/52* (2015.11); *Y02P 30/42* (2015.11)

(58) Field of Classification Search
CPC ................................................ B01J 29/7053; B01J 29/7607; B01J 29/7407; B01J 29/7807; B01J 29/047; B01J 29/89; C07C 1/20; C07C 2529/70; C07D 201/12; B01D 53/9418
See application file for complete search history.

(56) References Cited

U.S. PATENT DOCUMENTS

| | | | |
|---|---|---|---|
| 4,483,835 A | 11/1984 | Zones | |
| 4,503,023 A * | 3/1985 | Breck | B01J 29/06 |
| | | | 423/715 |
| 4,544,538 A | 10/1985 | Zones | |
| 7,056,490 B2 | 6/2006 | Harbuzaru et al. | |
| 2010/0078388 A1 | 4/2010 | Strohmaier et al. | |
| 2010/0119736 A1 | 5/2010 | Yan et al. | |
| 2015/0004094 A1 | 1/2015 | Schmidt et al. | |
| 2016/0346771 A1* | 12/2016 | Schmidt | B01J 20/10 |
| 2017/0113940 A1 | 4/2017 | Lobo et al. | |

OTHER PUBLICATIONS

Kim et al, :Methanol to Olefin Conversion over UZM-9 Zeolite: Effect of Transition Metal Ion Exchange on its Deactivation, Korean Chemical Engineering Reasearch, vol. 51(2) p. 181-188 (Year: 2013).*

Deka, "Selective Catalytic Reduction of NOx over Copper-Based Microporous Catalysts", (Year: 2013).*

Yahiro et al, Copper ion-exchanged zeolite catalysts in deNOx reaction Applied Catalysis 222 (2001) 163-181 (Year: 2001).*

Petrov, "Cu exchanged microporous titanium silicalite (TS-1) coated on polycrystalline mullite fibres as catalyst for the CO and NO conversion", Appluied Catalysis B 8 (1996) 9-31 (Year: 1996).*

Barrer et al, "Hydrothermal Chemistry of the Silicates. Part VIII. Lowtemperature Crystal Growth of Alruminosilicates, and of Some Gallium and Germnium Analogues.", HydrothermaL Chemistry of the Silicates. Part VIII., 195-208 (Year: 1959).*

Corma et al, "Supramolecular self-assembled molecules as organic directing agent for synthesis of zeolites", Nature vol. 431, pp. 287-290 (2004) (Year: 2004).*

Zones, "Translating new materials discoveries in zeolite research to commercial manufacture", Microporous Mesoporous Mater, Oct. 2011, 144, 1-8.

Zones et al., "Studies on the Role of Fluoride Ion vs Reaction Concentration in Zeolite Synthesis", The Journal of Physical Chemistry B, 2005, 109, 652-661.

Yilmaz et al., "Catalytic Applications of Zeolites in Chemical Industry", Top Catal, 2009, 52, 888-895.

Vermeiren et al., "Impact of Zeolites on the Petroleum and Petrochemical Industry", Top Catal, May 2009, 52, 1131-1161.

Tiscornia et al., "Preparation of ITQ-29 (Al-free zeolite A) membranes", Microporous Mesoporous Mater, 2008, 110, 303-309.

Sun et al., "A Dynamic Organic Structuring-Directing Agent for Pure-Silica-Zeolite AST and LTA Syntheses", Chinese Journal of Catalysis, Jan. 2012, vol. 33, Issue 1, 85-91.

Schmidt et al., "The synthesis of aluminophosphate and germanosilicate LTA using a triquatemary structure directing agent", Microporous Mesoporous Mater, 2014, 200, 132-139.

Schmidt et al., "Facile Preparation of Aluminosilicate RTH across a Wide Composition Range Using a New Organic-Structure-Directing Agent", Chemistry of Materials, Dec. 2014, 26, 7099-7105.

Pophale et al., "Computational Prediction of Chemically Synthesizable Organic Structure Directing Agents for Zeolites", Journal of Materials Chemistry A, 2013, 1 (23), 6750-6760.

Park et al., "Effects of cage shape and size of 8-membered ring molecular sieves on their deactivation in methanol-to-olefin (MTO) reactions", Applied Catalysis A: General, Jan. 2008, 339, 36-44.

Moliner et al., "Synthesis Strategies for Preparing Useful Small Pore Zeolites and Zeotypes for Gas Separations and Catalysis", Chemistry of Materials, 2014, 26, 246-258.

Lewis et al., "Experimental charge density matching approach to zeolite synthesis", Studies in Surface Science and Catalysis, Apr. 2004, 154, 364-372.

Julbe, "Zeolite Membranes—Synthesis, Characterization and Application, Chapter 6", Introduction to Zeolite Science and Practice—3rd Revised Edition,(Copyrights) 2007, 39 pages.

Hunt et al., "Pure-silica zeolite thin films by vapor phase transport of fluoride for low-k applications", Microporous and Mesoporous Materials, 2010, 128, 12-18.

Hunt et al., "Pure-silica LTA, CHA, STT, ITW, and -SVR thin films and powders for low-k applications", Microporous and Mesoporous Materials, 2010, 130, 49-55.

Huang et al., "Steam-stable hydrophobic ITQ-29 molecular sieve membrane with H2 selectivity prepared by secondary growth using Kryptofix 222 as SDA", Chemical Communications, Sep. 2010, 46, 7748-7750.

Huang et al., "Facile and reproducible synthesis of ITQ-29 zeolite by using Kryptofix 222 as the structure directing agent", Microporous and Mesoporous Materials, May 2010, 130, 352-356.

Fayad et al., "A Rational Approach to the Ionothermal Synthesis of an AlPO4 Molecular Sieve with an LTA-Type Framework", Angewandte Chemie International Edition, Jun. 2010, vol. 49, Issue 27, 4585-45888.

(56) References Cited

OTHER PUBLICATIONS

Corma et al., "Supramolecular self-assembled molecules as organic directing agent for synthesis of zeolites", Nature, Sep. 2004, 431, 287-290.
Breck et al., "Crystalline Zeolites. I. The Properties of a New Synthetic Zeolite, Type A", Journal of the American Chemical Society, Dec. 1956, vol. 78, Issue 23, 5963-5972.

* cited by examiner

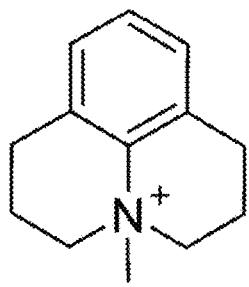
FIG. 1(A)
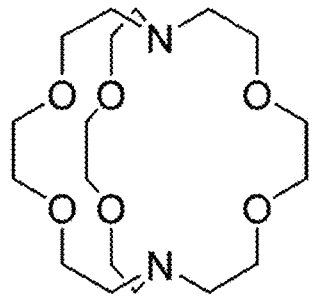
FIG. 1(B)
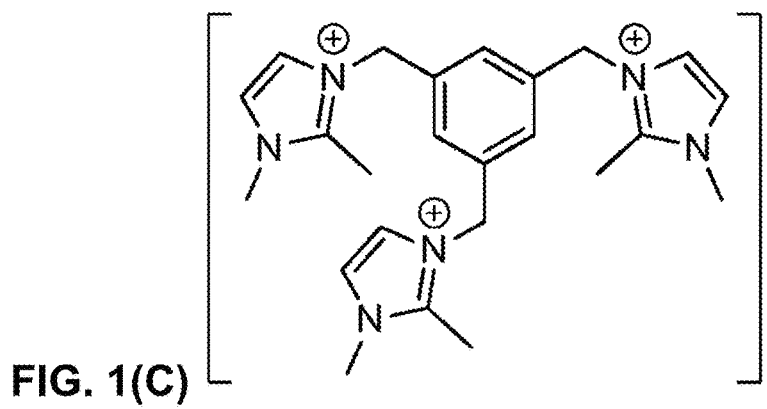
FIG. 1(C)
FIG. 2
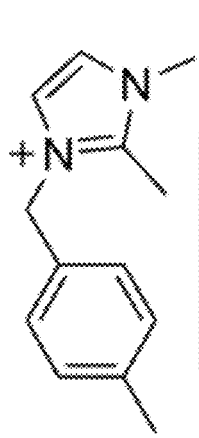
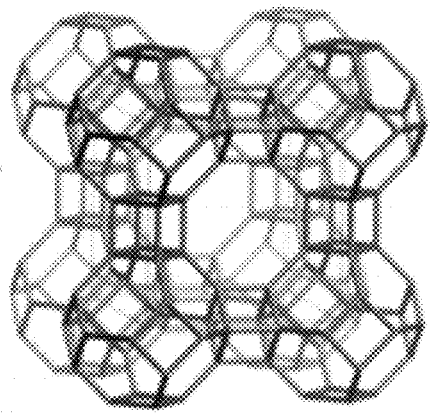

METHODS TO PRODUCE MOLECULAR SIEVES WITH LTA TOPOLOGY AND COMPOSITIONS DERIVED THEREFROM

CROSS REFERENCE TO RELATED APPLICATIONS

This application is a divisional application of U.S. patent application Ser. No. 15/063,867, filed Mar. 8, 2016, which claims priority to U. S. Patent Application Ser. Nos. 62/131,116 filed Mar. 10, 2015 and 62/204,876, filed Aug. 13, 2015, the contents of which are incorporated by reference herein in their entireties for all purposes.

TECHNICAL FIELD

The present disclosure is directed to producing molecular sieves with LTA topology using organic structure directing agents (OSDAs), and the compositions and structures resulting from these methods. The methods produce and the compositions comprising pure silicate and substituted silicate (e.g., aluminosilicate, germanosilicate, and titanosilicate) LTA products.

BACKGROUND

Microporous materials are crystalline solids formed from three-dimensional networks of oxide tetrahedra that contain pores (less than 2 nm) and cages that allow for shape-selective ion exchange, separations, and catalysis. These materials often exhibit robust hydrothermal stability that allows their application under demanding process conditions such as fluidized catalytic cracking, exhaust gas emissions and treatment of toxic waste. Over 200 different microporous material frameworks have been identified, but of these less than 20 have been commercialized, and the market is dominated by only a few frameworks. Despite this seeming barrier to market entry, the demand to innovate in these materials remains high as there is often only a single framework and composition that deliver optimal performance in a given application. In recent years, microporous materials with pore diameters limited by 8-membered rings have received increased attention as they demonstrate good activity and hydrothermal stability for high demand applications such as the methanol-to-olefins (MTO) reaction (SAPO-34) and the reduction of $NO_x$ in emissions (SSZ-13).

Zeolite A (Linde Type A, framework code LTA) is one of the most used zeolites in separations, adsorption, and ion exchange. This structure contains large spherical cages (diameter~11.4 Å) that are connected in three dimensions by small 8-membered ring (8MR) windows with a diameter of 4.1 Å. LTA is normally synthesized in hydroxide media in the presence of sodium with Si/Al~1. By changing the cation, the limiting diameter of the 8MR windows can be tuned, creating the highly used series of adsorbents 3A (potassium form, 2.9 Å diameter), 4A (sodium form, 3.8 Å diameter) and 5A (calcium form, 4.4 Å diameter) that are used to selectively remove species such as water, $NH_3$, $SO_2$, $CO_2$, $H_2S$, $C_2H_4$, $C_2H_6$, $C_3H_6$ and other n-paraffins from gases and liquids. While LTA is used in vast quantities for the aforementioned applications, the low framework Si/Al ratio and subsequent poor hydrothermal stability limits its use under more demanding process conditions that are commonly found in catalytic applications. Strategies have been developed to increase the Si/Al up to 5.5 in hydroxide media using combinations of organic structure directing agents (OSDAs), and this material has been shown to be active for the MTO reaction.

Pure-silica LTA (ITQ-29) was first reported in 2004 and was synthesized in fluoride media using a combination of methylated julolidine (4-methyl-2,3,6,7-tetrahydro-1H,5H-pyrido[3.2.1] quinolinium hydroxide (see FIG. 1(A))) and tetramethylammonium (TMA). Pure silica LTA showed an outstanding hydrothermal stability, and aluminum could also be introduced into the framework, making a material that showed activity for cracking as well as MTO. Pure-silica LTA has received considerable attention, especially for use in separations and as a membrane, since its hydrophobicity and small pore size show good discrimination for small molecules; it has also been studied as a low dielectric material. A method to synthesize germanosilicate LTA using a large polycyclic crown ether with the trade name Kryptofix 222 (see FIG. 1(B)) has been demonstrated. The material has 8MR openings that have 4.1 Å diameter and a spherical 3D network of 11.4 Å cavities. More recently, a method of preparing molecular sieves with LTA topologies have used triquaternary OSDAs, such as shown in FIG. 1(C).

In recent years there has been considerable interest in 8MR systems for catalysis and separations. Some of the most promising catalytic applications are the methanol to olefins (MTO) conversion and deNOx. Other 8MR materials of interest are LEV, CHA and AFX. It has been found that the cage size and connectivity are critical in determining the product distribution for these reactions in 8MR systems. LTA possesses a unique cage size and will likely exhibit unique catalytic performance. However, in order to produce an aluminosilicate material with the necessary silicon to aluminum ratio for the MTO reaction, a complicated OSDA is required, as shown in FIGS. 1(A-C). The nature of the organic makes it unlikely this material could be used in commercial production. The SDA-free syntheses of LTA can only be made at low Si/Al ratios and are less than optimal for catalysis.

The present invention is directed to addressing at least some of the shortcomings of the existing art.

SUMMARY

The present invention is directed to the use of benzyl-3H-imidazol-1-ium cations, one example being shown in FIG. 2, to prepare zeolites having LTA topologies, and the novel materials derived from these processes.

The disclosure provided certain embodiments directed to processes of making silicate compositions of a LTA topology, each process comprising hydrothermally treating an aqueous composition comprising:

(a) a source of a silicon oxide;

(b) an optional source of aluminum oxide;

(c) an optional source of germanium oxide;

(d) an optional source of titanium oxide;

(e) an optional source of one or more of boron oxide, gallium oxide, hafnium oxide, iron oxide, tin oxide, titanium oxide, indium oxide, vanadium oxide, zinc oxide, zirconium oxide, or combination or mixture thereof;

(f) a mineralizing agent; and (g) an organic structure directing agent (OSDA) comprising a substituted benzyl-3H-imidazol-1-ium cation of Formula (I):

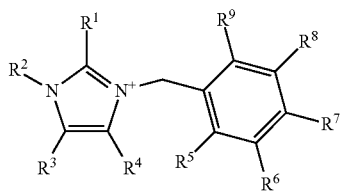

(I)

under conditions effective to crystallize a crystalline microporous solid of LTA topology;

wherein $R^1$, $R^2$, and $R^7$ are independently $C_{1-3}$ alkyl;

$R^3$, $R^4$, $R^5$, $R^6$, $R^8$, and $R^9$ are independently H or $C_{1-3}$ alkyl; and the substituted benzyl-3H-imidazol-1-ium cation has an associated bromide, chloride, fluoride, iodide, nitrate, or hydroxide anion. In certain aspects of the disclosure, the OSDA may comprise additional organic materials known to crystalline microporous solid of LTA topology. In other aspects of the disclosure, the aqueous composition comprises seeds having LTA topology.

The nature of the sources of the various oxides and their ratio ranges, the nature of the mineralizing agent, and the hydrothermal heating conditions are also disclosed as separate embodiments. Depending on the specific sources of metal or metalloid oxides, the processes can be used to prepare pure- and optionally substituted silicates, aluminosilicates, germanosilicates, and/or titanosilicates having an LTA topology.

Certain subset embodiments of the OSDAs are also disclosed. In one such embodiment, the OSDA comprises a 2,3-dimethyl-1-(4-methyl-benzyl)-3H-imidazol-1-ium cation of Formula (IB):

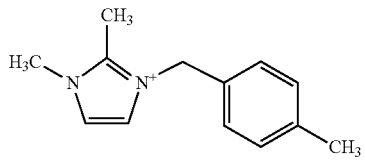

(IB)

In other embodiments, the processes further comprise isolating the crystalline microporous silicate solids of LTA topology and in some cases, further processing these isolated crystalline solids. In several cases, these processes include process steps to remove at least a portion, and preferably substantially all, of the OSDA occluded in the pores of the isolated solids. In some embodiments, this further processing is done in the presence of an alkali, alkaline earth, transition metal, rare earth metal, ammonium or alkylammonium salts (anions including halide, preferable chloride, nitrate, sulfate, phosphate, carboxylate, or mixtures thereof) to form a dehydrated or an OSDA-depleted product. In other aspects, these salts are added in a separate step from the removal of the OSDA.

Associated to these processes are the analogous compositions used in the processes. These embodiments of the compositions also specifically defined on terms of the nature of the OSDA, the ratios of the various components, and the processing conditions. Still other embodiments provide for crystalline microporous solids having pores at least some of which are occluded with the various 1-benzyl-3-alkyl-3H-imidazol-1-ium OSDAs described herein. Other embodiments include those where the pores are substantially or completely OSDA-depleted.

The products of the hydrothermal treating may be isolated and subjected to one or more of further processing conditions. Such treatments include:

(a) contacting the isolated crystalline microporous solid with ozone or other oxidizing agent at a temperature in a range of 100° C. to 200° C.; and (b) heating the isolated crystalline microporous solid at a temperature in a range of from about 200° C. to about 600° C. in the presence of an alkali, alkaline earth, transition metal, rare earth metal, ammonium or alkylammonium salts;

in each case for a time sufficient to form a dehydrated or an OSDA-depleted crystalline microporous product. Certain sub-embodiments describe specific aspects of these treatments.

These dehydrated or OSDA-depleted crystalline microporous products may be further treated with an aqueous ammonium or metal cation salt and/or with at least one type of transition metal or transition metal oxide.

Various embodiments disclose the compositions prepared by any one of the processes embodiments. These include compositions which may be described as:

(a) compositions comprising the aqueous compositions used in the hydrothermal treatments together with a compositionally consistent crystalline microporous aluminosilicate product, the compositionally consistent crystalline microporous products containing the OSDA used in their preparation occluded in their pores;

(b) the isolated crystalline microporous products which contain the 1-benzyl-3-alkyl-3H-imidazol-1-ium cations of Formula (I) occluded in their pores; and (c) the crystalline microporous products which have been dehydrated or from which the OSDAs have been substantially depleted from their pores and/or which have been post-treated to add salts, metals, or metal oxides into the pores of the crystalline microporous products.

In other embodiments, the crystalline microporous solids are described in terms of certain physical characteristics of the aluminosilicate solids, for example with respect to XRD patterns, $^{29}$Si MAS NMR spectra, $^{27}$Al MAS NMR spectra, $N_2$ or argon physisorption isotherms, and thermogravimetric analysis (TGA) data.

Still other embodiments include those in which the disclosed compositions, either as simple or chemically modified silicate frameworks, are used in an array of catalytic or separation processes.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods of making and methods of using, processes, devices, and systems disclosed. In addition, the drawings are not necessarily drawn to scale. In the drawings:

FIGS. 1(A-C) show previously the only known OSDAs for synthetic preparation of LTA-type materials: OSDA for the preparation of ITQ-29 (FIG. 1(A)) and OSDA for the preparation of germanosilicate LTA (FIG. 1(B)). FIG. 1(C) is another OSDA used in preparing molecular sieves with LTA topologies.

FIG. 2 shows general flow summary for the disclosed systems.

DETAILED DESCRIPTION OF ILLUSTRATIVE EMBODIMENTS

Figure 3:
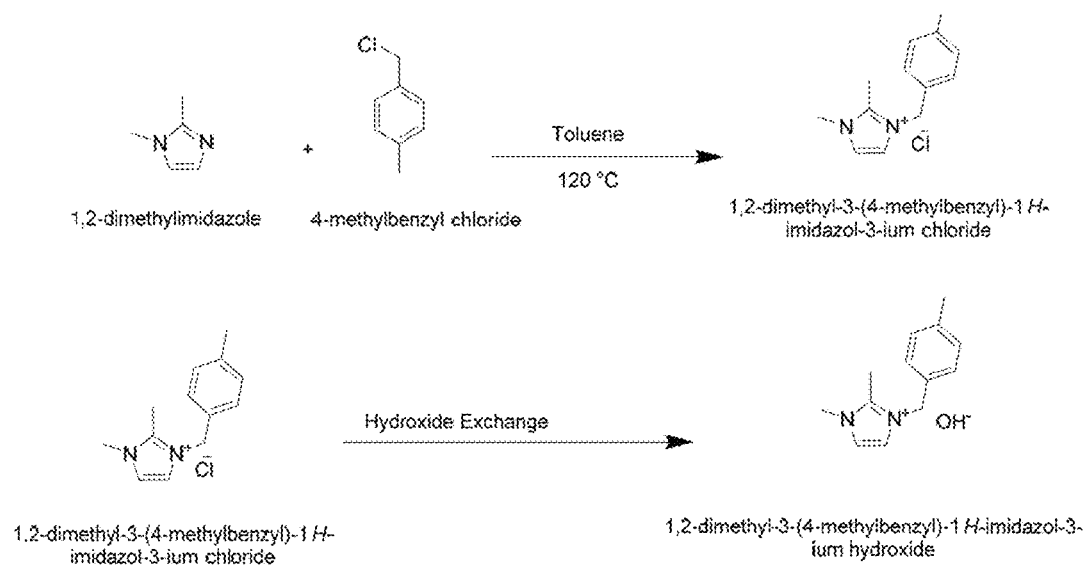
FIG. 3 shows synthetic scheme for the preparation of 1,2-dimethyl-3-(4-methyl-benzyl)-1H-imidazol-3-ium cations (chloride and hydroxide salts).

The present invention is directed to methods of producing crystalline pure-silica and heteroatom LTA frameworks, under conditions typical for fluoride-mediated microporous materials syntheses. Embodiments of the disclosure include methods of making and using such crystalline materials and compositions comprising these structures, both as-made and as further processed. These LTA materials, particularly the aluminosilicate LTA material is shown to be an active catalyst for the MTO reaction and shows interesting product selectivities compared to other 8MR materials. Germanosilicates and titanosilicate, the latter being a Lewis acidic LTA, can also be prepared using this method and itself may have possible applications where the 8MR ring and large, spherical cage size and may show advantages over larger pore materials.

The present invention may be understood more readily by reference to the following description taken in connection with the accompanying Figures and Examples, all of which form a part of this disclosure. It is to be understood that this invention is not limited to the specific products, methods, processes, conditions or parameters described or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this specification, claims, and drawings, it is recognized that the descriptions refer to compositions and processes of making and using said compositions. That is, where the disclosure describes or claims a feature or embodiment associated with a composition or a method of making or using a composition, it is appreciated that such a description or claim is intended to extend these features or embodiment to embodiments in each of these contexts (i.e., compositions, methods of making, and methods of using).

Terms

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. Similarly, unless otherwise specified, a given value carries with it the term "about" as an independent embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others.

The transitional terms "comprising," "consisting essentially of" and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method or process steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents), also provide, as embodiments, those which are independently described in terms of "consisting of" and "consisting essentially of" For those embodiments provided in terms of "consisting essentially of" the basic and novel characteristic(s) of a process is the ability to provide the named LTA compositions using the named OSDAs under conditions favoring the stable formation of the LTAS compositions, without the necessary need for other ingredients, even if other such components are present.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are described herein.

Unless otherwise stated, ratios or percentages are intended to refer to mole percent or atom percent, as appropriate.

Throughout this specification, words are to be afforded their normal meaning, as would be understood by those skilled in the relevant art. However, so as to avoid misunderstanding, the meanings of certain terms will be specifically defined or clarified.

"Lower alcohols" or lower alkanes refer to alcohols or alkanes, respectively, having 1-10 carbons, linear or branched, preferably 1-6 carbon atoms and preferably linear. Methanol, ethanol, propanol, butanol, pentanol, and hexanol are examples of lower alcohols. Methane, ethane, propane, butane, pentane, and hexane are examples of lower alkanes.

The terms "oxygenated hydrocarbons" or "oxygenates" as known in the art of hydrocarbon processing to refer to components which include alcohols, aldehydes, carboxylic acids, ethers, and/or ketones which are known to be present in hydrocarbon streams or derived from biomass streams other sources (e.g. ethanol from fermenting sugar).

The terms "separating" or "separated" carry their ordinary meaning as would be understood by the skilled artisan, insofar as they connote physically partitioning or isolating the product material from other starting materials or co-products or side-products (impurities) associated with the reaction conditions yielding the material. As such, it infers that the skilled artisan at least recognizes the existence of the product and takes specific action to separate or isolate it from starting materials and/or side- or byproducts. Absolute purity is not required, though it is preferred.

Unless otherwise indicated, the term "isolated" means physically separated from the other components so as to be free of at least solvents or other impurities, such as starting materials, co-products, or byproducts. In some embodiments, the isolated crystalline materials, for example, may be considered isolated when separated from the reaction mixture giving rise to their preparation, from mixed phase co-products, or both. In some of these embodiments, for example, pure silicates, aluminosilicates, germanosilicates, or titanosilicates (or structures containing incorporated OSDAs) can be made directly from the described methods. In some cases, it may not be possible to separate crystalline phases from one another, in which case, the term "isolated" can refer to separation from their source compositions.

"Optional" or "optionally" means that the subsequently described circumstance may or may not occur, so that the description includes separate embodiments where the circumstance occurs and embodiments where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present. Similarly, the phrase "optionally isolated" means that the target material may or may not be separated from other materials used or generated in the method, and, thus, the description includes separate embodiments where the target material is separated and where the target material is not separated, such that subsequence steps are conducted on isolated or in situ generated product.

The terms "method(s)" and "process(es)" are considered interchangeable within this disclosure.

As used herein, the term "crystalline microporous solids" or "crystalline microporous silicate or heteroatom-containing silicate solids," sometimes referred to as "molecular sieves," are crystalline structures having very regular pore structures of molecular dimensions, i.e., under 2 nm. The term "molecular sieve" refers to the ability of the material to selectively sort molecules based primarily on a size exclusion process. The maximum size of the species that can enter the pores of a crystalline microporous solid is controlled by the dimensions of the channels. These are conventionally defined by the ring size of the aperture, where, for example, the term "8-MR" or "8-membered ring" refers to a closed loop that is typically built from eight tetrahedrally coordinated silicon, or heteroatoms and 8 oxygen atoms. These rings are not necessarily symmetrical, due to a variety of effects including strain induced by the bonding between units that are needed to produce the overall structure, or coordination of some of the oxygen atoms of the rings to cations within the structure.

The term "silicate" refers to any composition including silicate (or silicon oxide) within its framework. It is a general term encompassing, for example, pure-silica (i.e., absent other detectable metal oxides within the framework), aluminosilicate, borosilicate, germanosilicate, or titanosilicate structures. The term "zeolite" refers to an aluminosilicate composition that is a member of this family. The term "aluminosilicate" refers to any composition including silicon and aluminum oxides within its framework. In some cases, either of these oxides may be substituted with other oxides. "Pure aluminosilicates" are those structures having no detectable other metal oxides in the framework. As long as the framework contains silicon and aluminum oxides, these substituted derivatives fall under the umbrella of aluminosilicates. Similarly, the term "germanosilicate" refers to any composition including silicon and germanium oxides within its framework. Such germanosilicate may be "pure-germanosilicate (i.e., absent other detectable metal oxides within the framework) or optionally substituted. Similarly, the term "titanosilicate" refers to any composition including silicon and titanium oxides within its framework. Such titanosilicate may be "pure-titanosilicate (i.e., absent other detectable metal oxides within the framework) or optionally substituted. When described as "optionally substituted," the respective framework may contain aluminum, boron, gallium, germanium, hafnium, iron, tin, titanium, indium, vanadium, zirconium, or other atoms substituted for one or more of the atoms not already contained in the parent framework.

The present disclosure describes and is intended to lay claim to methods of making crystalline compositions having LTA topologies, the compositions themselves, and methods of using these crystalline compositions. The structural features associated with the LTA topology are well-understood by those skilled in the art and are summarized, for example, in the Database of Zeolite Structures, maintained by the International Zeolite Association (IZA-SC). The most recently available Database at the timing of this disclosure is incorporated by reference for its descriptions of these topologies. Also as described elsewhere as well, it should be appreciated that any embodied feature described for one of these categories (i.e., compositions and methods of making or using) is applicable to all other categories.

Processes of Preparing Crystalline Compositions

Certain embodiments of the present disclosure include process for preparing crystalline microporous silicate compositions having an LTA topology, each process comprising hydrothermally treating an aqueous composition comprising:
  (a) a source of a silicon oxide;
  (b) an optional source of aluminum oxide;
  (c) an optional source of germanium oxide;
  (d) an optional source of titanium oxide;
  (e) an optional source of one or more of boron oxide, gallium oxide, hafnium oxide, iron oxide, tin oxide, titanium oxide, indium oxide, vanadium oxide, zinc oxide, zirconium oxide, or combination or mixture thereof;
  (f) a mineralizing agent; and
  (g) an organic structure directing agent (OSDA) comprising a substituted benzyl-3H-imidazol-1-ium cation of Formula (I):

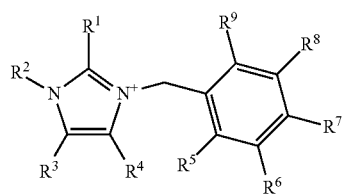

(I)

under conditions effective to crystallize a crystalline microporous solid of LTA topology;
wherein
$R^1$, $R^2$, and $R^7$ are independently $C_{1-3}$ alkyl (i.e., methyl, ethyl, n-propyl, or iso-propyl);
$R^3$, $R^4$, $R^5$, $R^6$, $R^8$, and $R^9$ are independently H or $C_{1-3}$ alkyl.

The counterion to the substituted benzyl-3H-imidazol-1-ium cation in Formula (I) is generally a bromide, chloride, fluoride, iodide, or hydroxide ion, but the OSDA may be added also to the composition as an acetate, nitrate, or sulfate. In some embodiments, the quaternary cation has an associated fluoride or hydroxide ion, preferably substantially free of other halide counterions. In separate embodiments, the associated anion is hydroxide.

The process (and associated compositions) may include the use of substituted benzyl-3H-imidazol-1-ium cation of Formula (I), wherein one or more of $R^1$, $R^2$, and $R^7$ are independently methyl or ethyl. In other embodiments, one or more of $R^1$, $R^2$, and $R^7$ are independently methyl. In still other embodiments, all of $R^1$, $R^2$, and $R^7$ are methyl.

Additionally, in some embodiments, one or more of $R^3$, $R^4$, $R^5$, $R^6$, $R^8$ and $R^9$ are independently H or methyl. In other embodiments, one or more of $R^3$, $R^4$, $R^5$, $R^6$, $R^8$ and $R^9$ are independently H or methyl. In other embodiments, all of $R^3$, $R^4$, $R^5$, $R^6$, $R^8$ and $R^9$ are H. For example, in certain aspects of these embodiments, the OSDA comprises a 2,3-dialkyl-1-(4-alkyl-benzyl)-3H-imidazol-1-ium cation of Formula (IA):

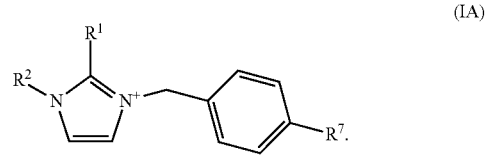

(IA)

The OSDA may also comprise a 2,3-dimethyl-1-(4-methyl-benzyl)-3H-imidazol-1-ium cation of Formula (IB):

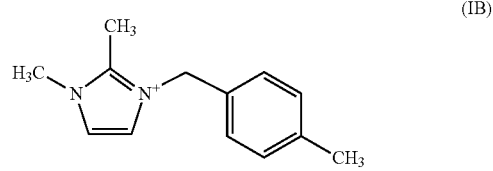

(IB)

(2,3-Dimethyl-1-(4-methyl-benzyl)-3H-imidazol-1-ium)

In some embodiments, the substituted benzyl-3H-imidazol-1-ium cation can be used in conjunction with lesser amounts of other OSDAs known to affect the formation of LTA-type topologies, for example, the structures shown in FIG. 1(A-C) (i.e., tetra-alkyl, especially tetramethyl, ammonium salts, methylated julolidine, polycyclic crown ethers like Kryptofix 222, or Triquats). In some embodiments, the relative molar ratio of these other OSDA (either individually or collectively) to the present optionally substituted benzyl-3H-imidazol-1-ium cation is in a range of from 0 to 0.05, from 0.05 to 0.1, from 0.1 to 0.15, from 0.15 to 0.2, from 0.2 to 0.25, from 0.25 to 0.3, from 0.3 to 0.35 to 0.4, from 0.4 to 0.45, from 0.45 to 0.5, or a range combining any two or more of these ranges, for example, from 0 to 0.15.

As described above, the hydrothermal processes for preparing the crystalline microporous silicate solids of LTA topology requires, inter alfa: (a) a source of a silicon oxide. This source of silicon oxide may comprise a silicate, silica hydrogel, silicic acid, fumed silica, colloidal silica, tetraalkyl orthosilicate, a silica hydroxide or combination thereof. Sodium silicate or tetraorthosilicates are preferred sources. The sources of silicon oxide may be amorphous (i.e., the XRD pattern of the solid showing little or no structure), microcrystalline (i.e., the XRD pattern of the solid showing broadened reflectance peaks indicative of a small degree of long range order), or crystalline (i.e., the XRD pattern of the solid showing well defined and sharp reflectance peaks). Any of the silicates (or heretoatom substituted silicates) may be of a topology or composition different than the topology or composition of the intended product (e.g., different than the LTA topology eventually prepared and/or isolated). In other embodiments, the silicate is the same topology or composition as the topology or composition of the intended product, for example, acting as seeds. For example, the use of LTA silicate seeds has proven to be useful in the formation of aluminosilicate LTA structures (see Examples).

Where the aqueous composition is free from any of the optional sources of metal oxides, the process yields crystalline microporous pure-silicate materials of LTA topology, the term "pure" reflecting the absence of all but the inevitable impurities present in the sources of silicon oxides. In independent embodiments, the aqueous composition to be hydrothermally treated (or being hydrothermally treated) comprises each and every individual or combination optional sources of the metal oxides and the process yields crystalline microporous silicate LTA solids of the corresponding substituted framework.

Within this general description, the hydrothermal processes for preparing the crystalline microporous aluminosilicate solids of LTA topology requires, inter alfa: (a) a source of a silicon oxide; and (b) a source of aluminum oxide, the resulting crystalline microporous solid being characterized as an aluminosilicate. In some embodiments, the source of aluminum oxide is or comprises an alkoxide, hydroxide, or oxide of aluminum, a sodium aluminate, an aluminum siloxide, an aluminosilicate, or combination thereof. In some embodiments, a mesoporous or zeolite aluminosilicate material may be used as a source of both aluminum oxide and silicon oxide. For example, FAU type zeolites serve as useful precursors, for example in structures having Si/Al=2.6. In separate embodiments, the aqueous composition is absent of or contains any of the optional sources of the metal oxides. Where the composition contains only sources of aluminum and silicon oxides, the resulting crystalline material is typically characterized as a pure-aluminosilicate solid of LTA topology, again, the term "pure" reflecting the absence of all but the inevitable impurities present in the sources of aluminum and silicon oxides.

Many of the sources of the various metals or metalloids can be alkoxides. In those cases where the source of metal oxide is an alkoxide of a metal M, for example of formula M(OR)n, where n is the nominal valence of M, R is one or more alkyl groups of 1-6 carbon atoms, including methyl, ethyl, n-propyl, isopropyl, n-butyl, sec-butyl, tert-butyl, n-pentyl, isopentyl, hexyl Some of these compounds, for example Al(OR)$_3$, can form complicated bridging structures in solution, even before hydrolysis. In independent embodiments, the silicon alkoxide is tetraethyl orthosilicate (TEOS), the aluminum alkoxide is Al(i-OPr)$_3$, and the source of titanium alkoxide is Ti(O-butoxide)$_4$. In some cases, where compositionally appropriate, the source of the metal oxides may also comprise mixed metal oxides, hydroxides, or alkoxides, for example aluminosilicate, aluminum siloxide, aluminosilicate, germanosilicates, titanosilicates, etc. In some aspects, when mixed metal oxides are used, mixed oxide sources may be compositionally or topologically different than the targeted LTA product topology. In other aspects, the mixed oxide sources may be compositionally or topologically the same as the targeted LTA product topology, for example if uses as seeds; for example, where the AlSi-LTA, GeSi-LTA, or TiSi-LTA are seeded with Si-LTA seeds.

In still other embodiments, the aqueous composition comprises, inter alfa, (a) a source of a silicon oxide; and (c) a source of a germanium oxide. Where the only sources of metal oxide sources are sources of silicon and germanium oxides, the process yields pure germanosilicate solids of LTA topology, the term "pure" reflecting the absence of all but the inevitable impurities present in the sources of germanium and silicon oxides. Other embodiments provide for the presence of one or more of the sources of optional metal oxides, in which case the presence of one or more of the optional sources of metal may result in correspondingly substituted frameworks. Sources of germanium oxide can include alkali metal orthogermanates, $M_4GeO_4$, containing discrete $GeO_4^{4-}$ ions, $GeO(OH)_3^-$, $GeO_2(OH)_2^{2-}$, $[(Ge(OH)_4)_8(OH)_3]^{3-}$ or neutral solutions of germanium dioxide contain $Ge(OH)_4$, or alkoxide or carboxylate derivatives thereof.

In a similar fashion, in some embodiments, the aqueous composition comprises, inter alfa, (d) a source of a titanium oxide, admixed with the source of silicon oxide. In some of these embodiments, the composition further comprises any one or more optional source of the optional metal oxides. Where the only sources of metal oxide sources are sources of silicon and titanium oxides, the process yields pure titanosilicate solids of LTA topology, the term "pure" reflecting the absence of all but the inevitable impurities present in the sources of titanium and silicon oxides. Other embodiments provide for the presence of one or more of the sources of optional metal oxides, in which case the presence of one or more of the optional sources of metal may result in correspondingly substituted frameworks. Sources of titanium oxide can include titanium alkoxides, oxides, or hydrated or hydrolyzed hydroxyl oxides.

Thus far, the processes (and associated compositions) have been described as in terms of the use or presence of a mineralizing agent. In some embodiments, the mineralizing agent comprises an aqueous alkali metal or alkaline earth metal hydroxide, thereby rendering these compositions alkaline. In certain aspects of this embodiment, the alkali metal or alkaline earth metal hydroxide, may include, for example, LiOH, NaOH, KOH, RbOH, CsOH, $Mg(OH)_2$, $Ca(OH)_2$, $Sr(OH)_2$, or $Ba(OH)_2$. LiOH, NaOH, or KOH appear to be preferred. In some cases, the pH of the water is in a range of from 7 to 7.5, from 7.5 to 8, from 8 to 8.5, from 8.5 to 9, from 9 to 9.5, from 9.5 to 10, from 10 to 11, from 11 to 12, from 12 to 13, from 13 to 14, or a range combining any two or more of these ranges. Under these conditions, the oxide precursors can be expected to be at least partially hydrated to their hydroxide forms.

In other embodiments, the mineralizing agent is or comprises a source of fluoride ion. Aqueous hydrofluoric acid is particularly suitable for this purpose, whether used as provided, or generated in situ by other conventional methods. Such sources of HF can include:

(a) aqueous ammonium hydrogen fluoride ($NH_4F.HF$);

(b) an alkali metal bifluoride salt (i.e., $MHF_2$, where $M^+$ is $Li^+$, $Na^+$, or $K^+$), or a combination thereof; or (c) at least one fluoride salt, such as an alkali metal, alkaline earth metal, or ammonium fluoride salt (e.g., LiF, NaF, KF, CsF, $CaF_2$, tetraalkyl ammonium fluoride (e.g., tetramethyl ammonium fluoride)) in the presence of at least one mineral acid that is stronger than HF (e.g., HCl, HBr, HI, $H_3PO_4$, $HNO_3$, oxalic acid, or $H_2SO_4$) and can react with fluorides to form HF in situ; or (d) a combination of two or more of (a)-(c). Volatile sources of fluoride (e.g., HF, $NH_4F$, or $NH_4F.HF$) are preferred.

The processes and compositions may also be defined in terms of the ratios of the individual ingredients. In certain embodiments, the molar ratio of the OSDA:Si is in a range of from 0.1 to 0.15, from 0.15 to 0.2, from 0.2 to 0.25, from 0.25 to 0.3, from 0.3 to 0.35, from 0.35 to 0.4, from 0.4 to 0.45, from 0.45 to 0.5, from 0.5 to 0.55, from 0.55 to 0.6, from 0.6 to 0.65, from 0.65 to 0.7, from 0.7 to 0.75, from 0.75 to 0.8, from 0.8 to 0.85, from 0.85 to 0.9, from 0.9 to 0.95, from 0.95 to 1, or a range combining any two or more of these ranges, for example from 0.4 to 0.6 or from 0.4 to 0.75. In this regard, the referenced OSDA is or comprises the substituted benzyl-3H-imidazol-1-ium cation of Formula (I). In those embodiments, where the substituted benzyl-3H-imidazol-1-ium cation is used in complement with the other OSDAs referenced elsewhere herein, the OSDA:Si ratio refers the total OSDA content.

In other embodiments, the molar ratio of water:Si is in a range of from about 2 to 3, from 3 to 4, from 4 to 5, from 5 to 6, from 6 to 7, from 7 to 8, from 8 to 9, from 9 to 10, from 10 to 11, from 11 to 12, from 12 to 13, from 13 to 14, from 14 to 15, from 15 to 16, from 16 to 17, from 17 to 18, from 18 to 19, from 19 to 20, or a range combining any two or more of these ranges, for example in a range of from about 2 to about 10, from about 4 to 10, or from 4 to 8.

In preparing the aluminosilicates, the molar ratio of Al:Si can be in a range of from 0 to 0.005, from 0.005 to 0.01, from 0.01 to 0.015, from 0.015 to 0.02, from 0.02 to 0.025, from 0.025 to 0.3, from 0.03 to 0.035 to 0.04, from 0.04 to 0.045, from 0.045 to 0.05, from 0.05 to 0.055, from 0.055 to 0.06, from 0.06 to 0.065, from 0.065 to 0.07, from 0.07 to 0.075 to 0.08, from 0.08 to 0.085, from 0.085 to 0.09, from 0.09 to 0.095, from 0.095 to 0.1, or a range combining any two or more of these ranges, for example, from 0.01 to 0.05 (molar range of Si:Al from 20 to 100)

In preparing the germanosilicates, the molar ratio of Ge:Si can be in a range of from 0 to 1 (Si/Ge=1 to infinity); in some embodiments, the molar ratio of Ge:Si is in a range of from 0 to 0.05, from 0.05 to 0.1, from 0.1 to 0.15, from 0.15 to 0.2, from 0.2 to 0.25, from 0.25 to 0.3, from 0.3 to 0.35, from 0.35 to 0.4, from 0.4 to 0.45, from 0.45 to 0.5, from 0.5 to 0.55, from 0.55 to 0.6, from 0.6 to 0.65, from 0.65 to 0.7, from 0.7 to 0.75, from 0.75 to 0.8, from 0.8 to 0.85, from 0.85 to 0.9, from 0.9 to 0.95, from 0.95 to 1, or a range combining any two or more of these ranges, for example, from 0.05 to 1 or from 0.05 to 0.5 (molar range of Si:Ge from 20 to 100)

In preparing the titanosilicates, the molar ratio of Ti:Si can be in a range of from 0 to 0.005, from 0.005 to 0.01, from 0.01 to 0.015, from 0.015 to 0.02, from 0.02 to 0.025, from 0.025 to 0.03, from 0.03 to 0.035, from 0.035 to 0.04, from 0.04 to 0.045, from 0.045 to 0.05, from 0.05 to 0.055, from 0.055 to 0.06, from 0.06 to 0.065, from 0.065 to 0.07, from 0.07 to 0.075, from 0.075 to 0.08, from 0.08 to 0.085, from 0.085 to 00.9, from 0.09 to 0.095, from 0.095 to 0.1, or a range combining any two or more of these ranges, for example, from 0.005 to 0.02 (molar range of Si:Ti from 50 to 200).

Where the mineralizing agent is a fluoride source, such as HF, the molar ratio of fluoride:Si may be in a range of from about 0.1 to 0.15, from 0.15 to 0.2, from 0.2 to 0.25, from 0.25 to 0.3, from 0.3 to 0.35, from 0.35 to 0.4, from 0.4 to 0.45, from 0.45 to 0.5, from 0.5 to 0.55, from 0.55 to 0.6, from 0.6 to 0.65, from 0.65 to 0.7, from 0.7 to 0.75, or a range combining any two or more of these ranges, for example in a range of from about 0.4 to about 0.6.

To this point, the processes have been defined in terms of conditions under conditions effective to crystallize a respective crystalline microporous solid of LTA topology. In light of the other teachings within this disclosure, this is believed to be a sufficient description. But in certain aspects of this, these conditions include treatment of the respective hydrothermally treated aqueous composition at a temperature in a range of from 100° C. to 110° C., from 110° C. to 120° C., from 120° C. to 125° C., from 125° C. to 130° C., from 130° C. to 135° C., from 135° C. to 140° C., from 140° C. to 145° C., from 145° C. to 150° C., from 150° C. to 155° C., from 155° C. to 160° C., from 160° C. to 165° C., from 165° C. to 170° C., from 170° C. to 175° C., from 175° C. to 180° C., from 180° C. to 185° C., from 185° C. to 190° C., from 190° C. to 195° C., from 195° C. to 200° C., or a range combining any two or more of these ranges, for example, from 120° C. to 160° C. In related embodiments, the times of this treatment, while dependent on the specific reaction conditions (e.g., temperatures and concentrations), can range from 3 to 40 days, preferably from 7 to 40 days. These ranges provide for convenient reaction times, though higher and lower temperatures and longer or shorter times may also be employed. This hydrothermal treating is also typically done in a sealed autoclave, at autogenous pressures. Some additional exemplary reaction conditions are provided in the Examples.

In some embodiments the reaction mixture can be subjected to mild stirring or rolling agitation during crystallization. It will be understood by a person skilled in the art that the as produced crystalline microporous solid s described herein can contain impurities, such as amorphous materials, or materials having framework topologies which do not coincide with the targeted or desired molecular sieve. During hydrothermal crystallization, the molecular sieve crystals can be allowed to nucleate spontaneously from the reaction mixture.

As described above, the use of crystals of the molecular sieve as seed material can result in decreasing the time necessary for complete crystallization to occur. In addition, seeding can lead to an increased purity of the product obtained by promoting the nucleation and/or formation of the molecular sieve over any undesired phases. When used as seeds, seed crystals are added in an amount between 0.01% and 10% of the mass of the total amount of oxide in the reaction mixture. The total amount of oxide refers to the total mass of oxides in the reaction mixture gel prior to heating, present as the oxides or oxide sources.

In some embodiments, silicate membranes or films can be formed by bringing an optionally porous support (e.g., comprising porous alumina, pretreated silicon wafers, or other organic or inorganic polymer capable of withstanding the hydrothermal treating conditions) in contact with the aqueous composition to be hydrothermally treated and maintaining the system under conditions to nucleate and/or grow a thin continuous film on the surface and/or in the pores of the support. In some embodiments, pre-nucleated seed crystals of LTA topology are deposited on the support (for example, by dipcoating the support into a suspension of seed crystals) before contacting with the aqueous compositions. Maintaining the systems under appropriate hydrothermal conditions provides membranes (as opposed to individual crystals) that are generally highly selective and appropriately permeable. Removing the OSDAs after the formation of the crystalline membranes or films can be accomplished by any of the post-treatments described elsewhere herein for these materials. Exemplary parallel systems have been described in H. K. Hunt, et al., *Microporous and Mesoporous Mat'ls.*, 128 (2010) 12-18 and H. K. Hunt, et al., *Microporous and Mesoporous Mat'ls.*, 130 (2010) 49-55, both of which are incorporated by reference in their entireties for all purposes.

Once the initially-formed crystalline microporous solids of LTA topology are prepared (e.g., including pure or substituted silicates, pure or substituted aluminosilicates, pure or substituted germanosilicates, or pure or substituted titanosilicates), further embodiments comprising isolating these solids. These crystalline solids may be removed from the reaction mixtures by any suitable means (e.g., filtration, centrifugation, etc. or simple removal of the membrane template) and dried. Such drying may be done in air or under vacuum at temperatures ranging from 25° C. to about 200° C. Typically, such drying is done at a temperature of about 100° C.

These crystalline microporous solids may be further modified, for example, by incorporating metals with the pore structures, either before or after drying, for example by replacing some of the cations in the structures with additional metal cations using techniques known to be suitable for this purpose (e.g., ion exchange). Such cations can include those of rare earth, Group 1, Group 2 and Group 8 metals, for example Ca, Cd, Co, Cu, Fe, Mg, Mn, Ni, Pt, Pd, Re, Sn, Ti, V, W, Zn and their mixtures.

Alternatively or additionally, the isolated crystalline solid may be subject to further processing, such further comprising heating the isolated crystalline microporous solid at a temperature in a range of from about 250° C. to 300° C., from 300° C. to 350° C., from 350° C. to 400° C., from 400° C. to about 450° C., or a range combining any two or more of these ranges, to form an OSDA-depleted product. The heating may be done in an oxidizing atmosphere, such as air or oxygen, or in the presence of other oxidizing agents. In other embodiments, the heating is done in an inert atmosphere, such as argon or nitrogen.

As used herein, the term "OSDA-depleted" (or composition having depleted OSDA) refers to a composition having a lesser content of OSDA after the treatment than before. In preferred embodiments, substantially all (e.g., greater than 90, 95, 98, 99, or 99.5 wt %) or all of the OSDA is removed by the treatment; in some embodiments, this can be confirmed by the absence of a TGA endotherm associated with the removal of the OSDA when the product material is subject to TGA analysis or the absence or substantial absence of C or N in elemental analysis (prior to heating, expect composition to comprise C, N, O, Si, Al, H).

In those embodiments where the processing involved heating, typical heating rates include is 0.1° C. to 10° C. per minute and or 0.5° C. to 5° C. per minute. Different heating rates may be employed depending on the temperature range. Depending on the nature of the calcining atmosphere, the materials may be heated to the indicated temperatures for periods of time ranging from 1 to 60 hours or more, to produce a catalytically active product.

Further processing of these materials, whether modified or not, may also comprise contacting the isolated crystalline microporous silicate solid with ozone or other oxidizing agent at a temperature in a range of 100° C. to 200° C. for a time sufficient to form an OSDA-depleted silicate product. In certain of these embodiments, the heating is done at a temperature of about 150° C. for a time sufficient to form an OSDA-depleted product. The ozone-treatment can be carried out in a flow of ozone-containing oxygen (typically for 6 hours or more. but shorter could be feasible). Practically any oxidative environment sufficient to remove the OSDA can be used, especially those already known for this purpose. Such environments, for example, can involve the use of organic oxidizers (alkyl or aryl peroxides or peracids) or inorganic peroxides (e.g., $H_2O_2$) (alkyl or aryl peroxides or peracids.

Further processing of these materials, whether modified or not, may also comprise, heating the isolated crystalline microporous silicate solid at a temperature in a range of from about 200° C. to about 600° C. in the presence of an alkali, alkaline earth, transition metal, rare earth metal, ammonium or alkylammonium salts (anions including halide, preferable chloride, nitrate, sulfate, phosphate, carboxylate, or mixtures thereof) for a time sufficient to form a dehydrated or an OSDA-depleted product. In certain of these embodiments, the heating is done in the presence of NaCl or KCl. In certain exemplary embodiments, the heating is done at a temperature in a range of from 500 to 600° C. In exemplary embodiments, the heating is done in either an oxidizing or inert atmosphere.

Once dehydrated or calcined, the dehydrated or OSDA-depleted crystalline microporous material may be treated with an aqueous ammonium or metal salt or may be treated under conditions so as to incorporate at least one type of alkaline earth metal or alkaline earth metal oxide or salt, or transition metal or transition metal oxide. In some embodiments, the salt is a halide salt. Where the salt is an ammonium salt, the resulting aluminosilicate may be simply protonated (in the hydrogen form). In other embodiments, the metal salt comprises $K^+$, $Li^+$, $Rb^+$, $Cs^+$:$Co^{2+}$, $Ca^{2+}$, $Mg^{2-}$, $Sr^{2+}$; $Ba^{2+}$; $Ni^{2+}$; $Fe^{2+}$. In other specific embodiments, the metal cation salt is a copper salt, for example, Schweizer's reagent (tetraamminediaquacopper dihydroxide, [Cu$(NH_3)_4(H_2O)_2$]$(OH)_2$]), copper(II) nitrate, or copper(II) carbonate.

The addition of a transition metal or transition metal oxide may be accomplished, for example by chemical vapor deposition or chemical precipitation. As used herein, the term "transition metal" refers to any element in the d-block of the periodic table, which includes groups 3 to 12 on the periodic table. In actual practice, the f-block lanthanide and actinide series are also considered transition metals and are called "inner transition metals. This definition of transition metals also encompasses Group 4 to Group 12 elements. In certain independent embodiments, the transition metal or transition metal oxide comprises an element of Groups 6, 7, 8, 9, 10, 11, or 12. In other independent embodiments, the transition metal or transition metal oxide comprises scandium, yttrium, titanium, zirconium, vanadium, manganese, chromium, molybdenum, tungsten, iron, ruthenium, osmium, cobalt, rhodium, iridium, nickel, palladium, platinum, copper, silver, gold, or mixtures. Fe, Ru, Os, Co, Rh, Ir, Ni, Pd, Pt, Cu, Ag, Au, and mixtures thereof are preferred.

Intermediate Reaction Compositions

As described herein, the as-formed and post-treated crystalline silicate compositions themselves are within the scope of the present disclosure and are considered to be independent embodiments of the present invention. All of the descriptions used to describe the features of the disclosed processes yield compositions which are separately considered embodiments. In an abundance of caution, some of these are presented here, but these descriptions should not be considered to exclude embodiments provided, or which naturally follow from other descriptions.

Included in these embodiments are compositions comprising the aqueous compositions used in the hydrothermal treatments together with the respective crystalline microporous silicate products, wherein the silicate products contain the respective OSDAs used in their preparation occluded in their pores.

For example, in some embodiments, the composition comprises:

(a) a source of a silicon oxide;
(b) an optional source of aluminum oxide;
(c) an optional source of germanium oxide;
(d) an optional source of titanium oxide;
(e) an optional source of one or more of boron oxide, gallium oxide, hafnium oxide, iron oxide, tin oxide, titanium oxide, indium oxide, vanadium oxide, zinc oxide, zirconium oxide, or combination or mixture thereof;
(f) a mineralizing agent; and
(g) an organic structure directing agent (OSDA) comprising a substituted benzyl-3H-imidazol-1-ium cation of Formula (I):

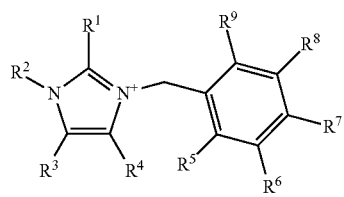

(I)

and
(h) a compositionally consistent crystalline microporous silicate solid of LTA topology;
wherein
$R^1$, $R^2$, and $R^7$ are independently $C_{1-6}$ alkyl, preferably $C_{1-3}$ alkyl;
$R^3$, $R^4$, $R^5$, $R^6$, $R^8$, and $R^9$ are independently H or $C_{1-3}$ alkyl.

The substituted benzyl-3H-imidazol-1-ium cation has an associated anion such as otherwise described herein as associated thereto.

As used herein, the term "compositionally consistent" refers to a crystalline silicate composition having a stoichiometry resulting from the crystallization of the of sources of oxides in the presence of substituted benzyl-3H-imidazol-1-ium cation; i.e., the OSDAs of Formula (I). In some of these embodiments, for example, this term reflects a composition which is the result of at least a partial progression of the hydrothermal treating process used to prepare these materials. Typically, these compositionally consistent crystalline microporous pure or optionally substituted silicate, pure or optionally substituted aluminosilicate, pure or optionally substituted germanosilicate, or pure or optionally substituted titanosilicate solids contain, occluded in their pores, the OSDA used to make them; i.e., the OSDA present in the associated aqueous compositions. All such compositions are considered within the scope of the present disclosure.

In separate embodiments, these compositionally consistent crystalline microporous silicate solids may be substantially free of the OSDAs used in the aqueous media; in such embodiments, the optionally substituted silicates may be used as seed material for the crystallization, also as described elsewhere herein.

These compositions may comprise any of the types, sources, and ratios of ingredients associated with a process described elsewhere herein, and may exist at any temperature consistent with the processing conditions described above as useful for the hydrothermal processing embodiments. It should be appreciated that this disclosure captures each and every of these permutations as separate embodiments, as if they were separately listed. In some embodiments, these compositions exist in the form of a suspension. In other embodiments, these compositions exist in the form of a gel.

Crystalline Microporous Compositions

In addition to the processing and process compositions, each of the crystalline microporous silicate products of LTA topology formed according to the methods described herein are also considered individual embodiments within the scope of the present invention. That is, each crystalline microporous product having LTA topology produced by any of the hydrothermal processing steps, or from any of the post-processing steps, is considered a separate embodiment of this disclosure. In preferred embodiments, the crystalline microporous silicate solid is preferably one of entirely LTA topology. Separate embodiments also provide that the crystalline microporous solid may also contain other structural phases or phase mixtures.

These isolated microporous silicate solid of LTA topology may contain any of the genera or specific substituted benzyl-3H-imidazol-1-ium cation OSDAs described herein occluded in their pores—i.e., the OSDAs of Formula (I) within the respective framework. Such solids independently include the pure and optionally substituted silicates, pure and optionally substituted aluminosilicates, pure and optionally substituted germanosilicates, and pure and optionally substituted titanosilicates having occluded OSDAs, the ODSAs including those of:

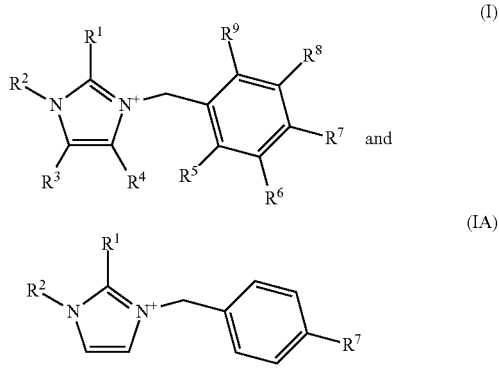

wherein $R^1$, $R^2$, $R^3$, $R^4$, $R^5$, $R^6$, $R^7$, $R^8$, and $R^9$ are defined in terms as otherwise described herein, including the structure:

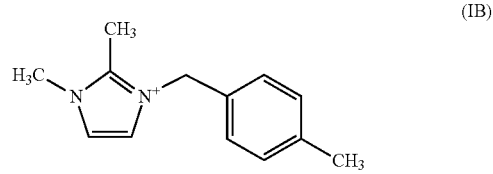

(IB)

In some embodiments, the isolated microporous silicate solid of LTA topology may be devoid or substantially devoid of such organic materials (the terms "devoid" and "substantially devoid" being quantitatively analogous to the term "OSDA depleted").

The presence of these OSDAs may be identified using, for example $^{13}C$ NMR or any of the methods defined in the Examples. It is a particular feature of the present invention that the cationic OSDAs retain their original structures, including their stereochemical conformations during the synthetic processes, these structures being compromised during the subsequent calcinations or oxidative treatments.

In some embodiments, where HF or other source of fluoride is used that the mineralizing agent, the pores may additionally comprise fluoride (as evidenced by $^{19}F$ NMR).

In certain embodiments, the aluminosilicates materials have a molar ratio of Si:Al in a range of from about from 5 to 6, from 6 to 8, from 8 to 10, from 10 to 14, from 14 to 18, from 18 to 22, from 22 to 26, from 26 to 30, from 30 to 34, from 34 to 38, from 38 to 42, from 42 to 44, from 44 to 46, from 46 to 50, from 50 to 100, from 100 to infinity (i.e., pure silica) or a range combining any two or more of these ranges, for example, from 12 to 42. In other embodiments, the titanosilicates have a molar ratio of Si:Ti of at least 25 (or Ti:Si≤0.02, or in a range of from about 50 to 100, from 100 to 150, from 150 to 250, from 250 to 500, from 500 to 1000, or a range combining any two or more of these ranges, for example, from 50 to 150.

The disclosed crystalline microporous silicate compositions include those which result from the post-treatment or further processing described in the processing section. These include those silicates which are in their hydrogen forms or have cations, metals or metal oxides within their pore structures. Accordingly, in certain embodiments, the microporous pure or substituted silicates, pure or substituted aluminosilicate, pure or substituted germanosilicate, or pure or substituted titanosilicate having LTA topology contain Li, Na, K, Rb, Cs, Be, Mg, Ca, Sr, Be, Al, Ga, In, Zn, Ag, Cd, Ru, Rh, Pd, Pt, Au, Hg, La, Ce, Pr, Nd, Pm, Sm, Eu, or $R_{4-n}N^+H_n$ cations, where R is alkyl, n=0–4 in at least some of their pores. In specific aspects of these embodiments, these pores contain NaCl or KCl.

Additional embodiments include those crystalline microporous solids having LTA topologies, at least some of whose pores transition metals, transition metal oxides, or salts, for example scandium, yttrium, titanium, zirconium, vanadium, manganese, chromium, molybdenum, tungsten, iron, ruthenium, osmium, cobalt, rhodium, iridium, nickel, palladium, platinum, copper, silver, gold, or mixtures thereof, each as a metal, oxide, or salt. In one specific embodiment, the pores of the silicate solids contain copper, as metal, oxide, or salt.

Figure 5:
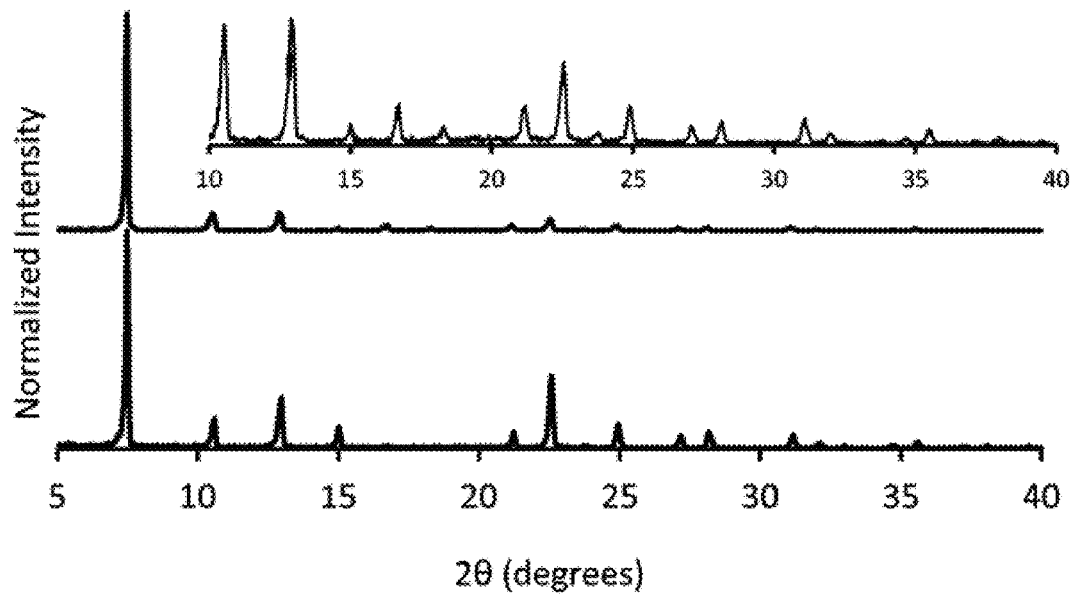
FIG. 5 shows powder X-ray diffraction patterns of as-made (lower) and calcined (upper) pure-silica LTA. The inset image is of the calcined material with the intensity increased to show the reflections more clearly.
Figure 7A:
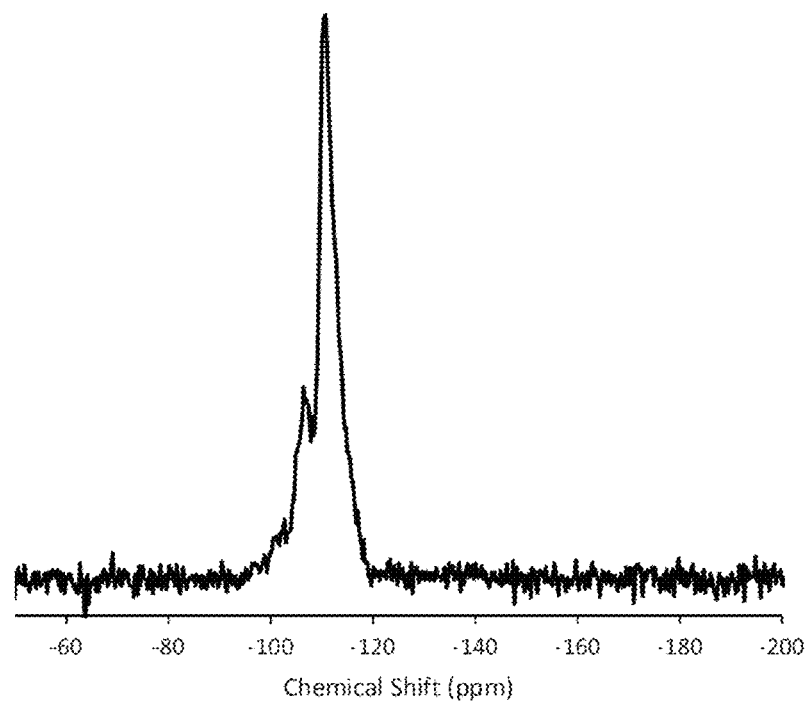
FIGS. 7(A-B) shows a solid state $^{29}$Si CPMAS NMR spectra of an as-made pure silica LTA (FIG. 7(A)) and a calcined pure silica LTA (FIG. 7(B)).
Figure 9A:
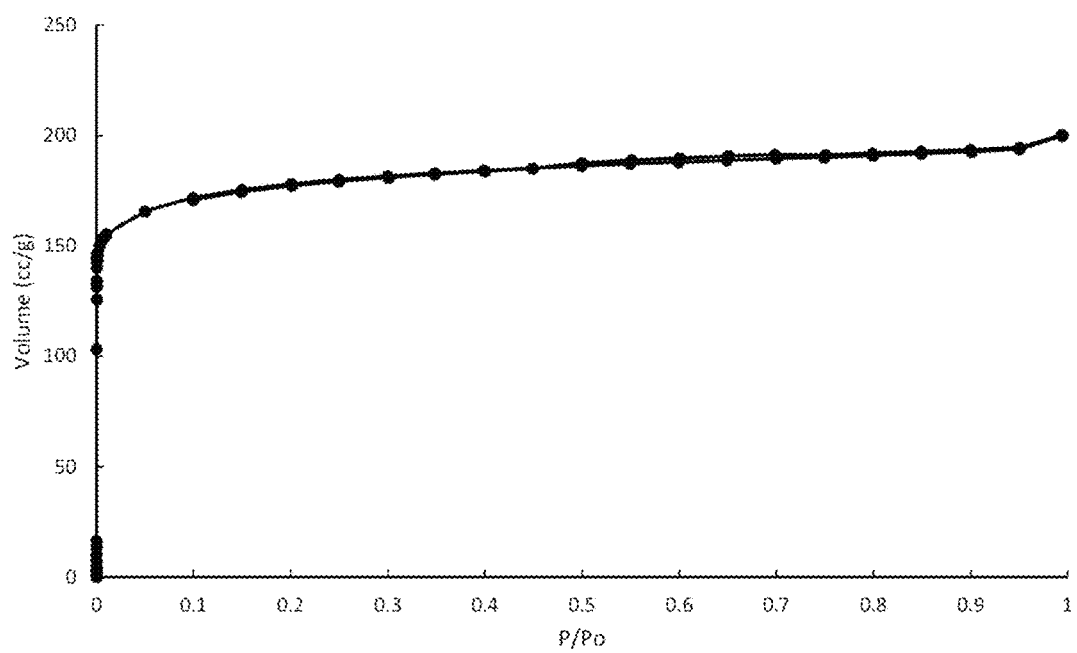
FIG. 9(A) shows a nitrogen adsorption isotherm data derived from calcined pure-silica LTA (t-plot micropore volume of 0.25 cc/g)
Figure 9B:
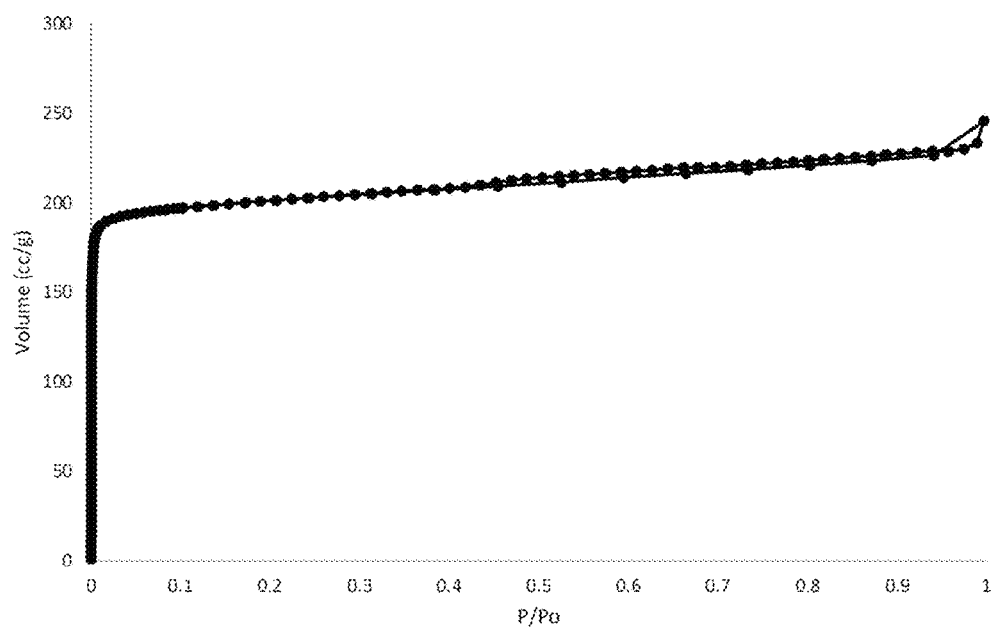
FIG. 9(B) shows an Argon adsorption isotherm of calcined pure-silica LTA.
Figure 9C:
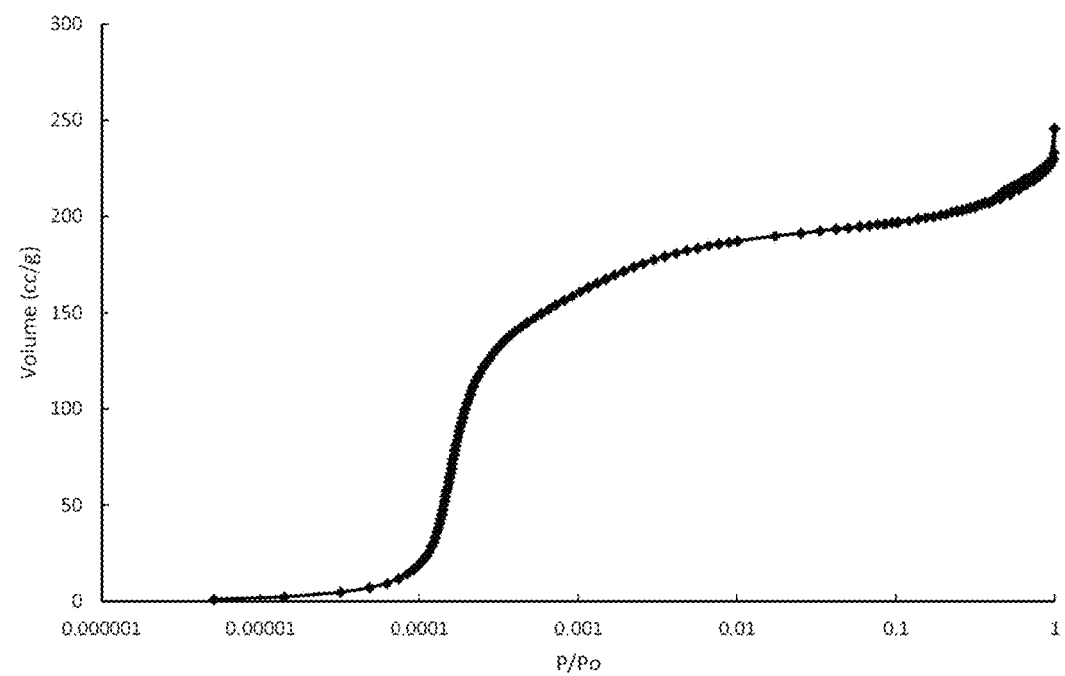
FIG. 9(C) shows a log plot argon adsorption isotherm of calcined pure-silica LTA.
Figure 12:
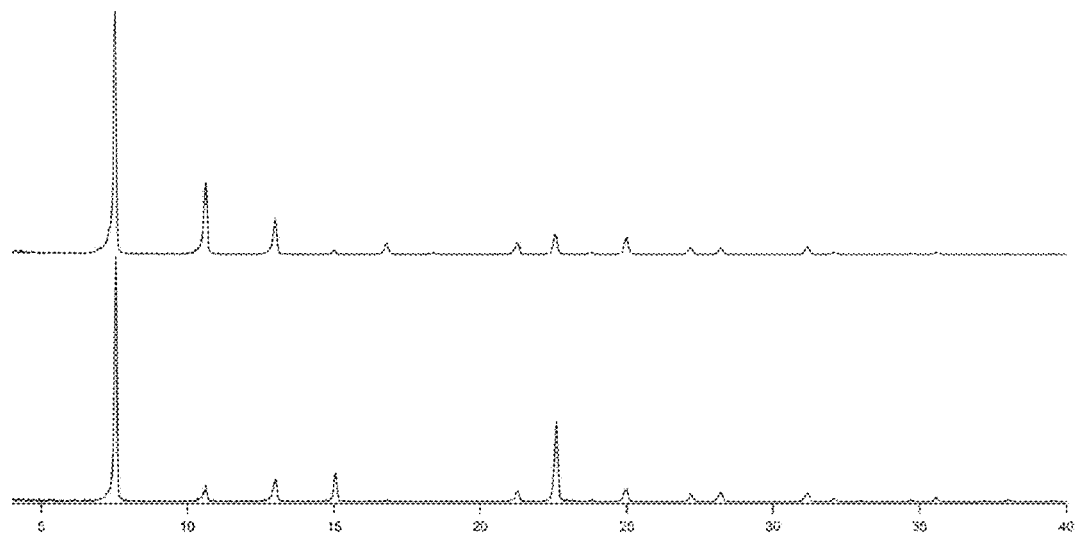
FIG. 12 shows PXRD traces of an aluminosilicate LTA, as-made (lower trace) and calcined (upper trace).
Figure 13A:
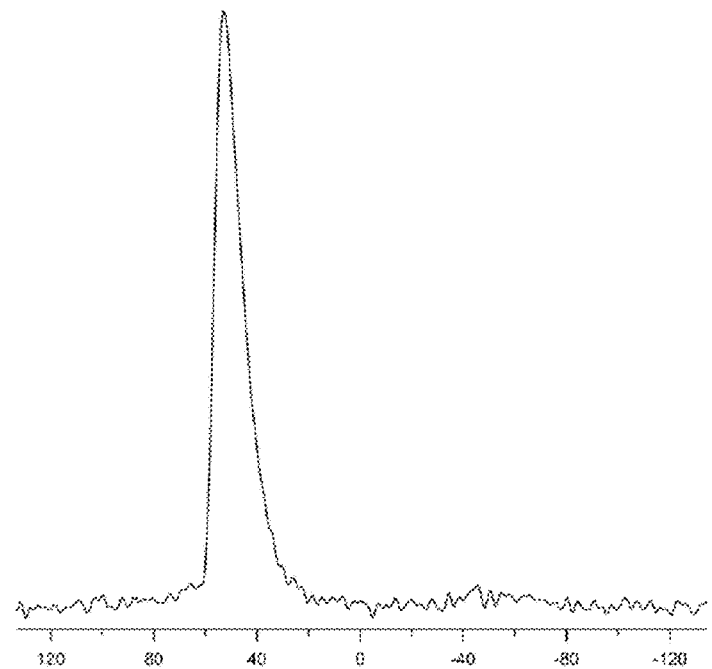
FIGS. 13(A-C) show solid state $^{27}$Al NMR of aluminosilicate LTAs: an as-made sample, from gel Si/Al=30.8 (FIG. 13(A)); a second as-made sample, from gel Si/Al=20 (FIG. 13(B)); and calcined sample of gel having Si/Al=20 (FIG. 13(C)). Spinning sidebands are marked with *.
Figure 14A:
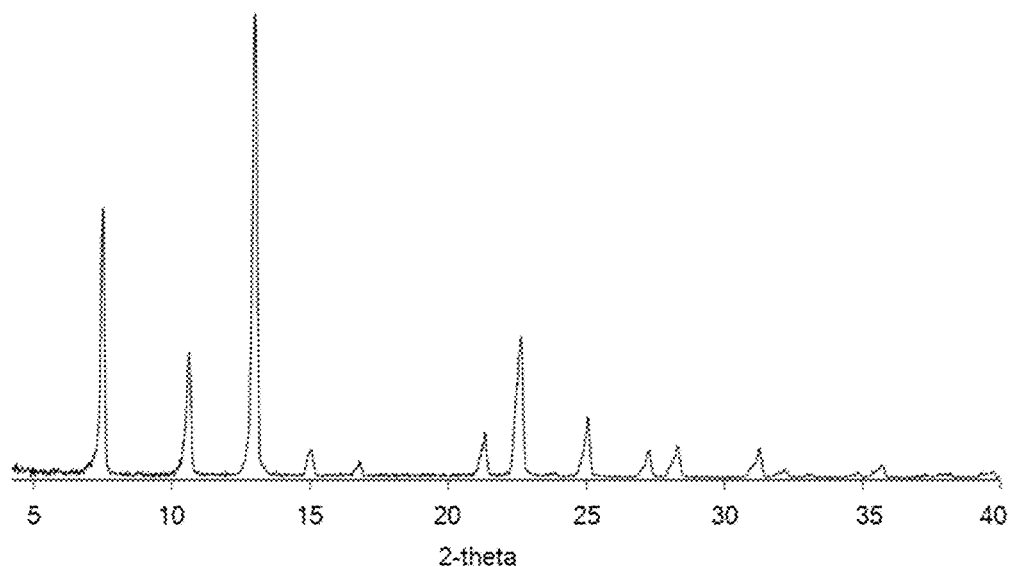
FIGS. 14(A-B) show PXRD traces for germanosilicates prepared from gels wherein the molar ratio of Si:Ge was 16:1 (FIG. 14(A)) and 8:1 (FIG. 14(B)).

The crystalline microporous silicate solids may also characterized by their physical properties. In specific embodiments, the crystalline microporous solid exhibits one or more of the following characteristics:

(a) an XRD pattern having at least the five major peaks substantially as provided in Table 2A or 2B;

(b) an XRD diffraction pattern the same as or consistent with any one of those shown in FIG. 5, FIG. 12, or FIG. 14(A) or (B);

(c) unit cell substantially the same as those shown in any one of Table 3-5;

(d) an $^{29}Si$ MAS spectrum the same as or consistent with either of those shown in FIG. 7(A) or (B);

(e) an $^{27}Al$ MAS spectrum the same as or consistent with either of those shown in FIG. 13(A), (B), or (C); and (f) an physisorption isotherm with $N_2$-gas or with argon the same as or consistent with any one of those shown in FIG. 9 (A-C).

Use of the Inventive Compositions—Catalysis

The crystalline microporous silicate solids, calcined, doped, or treated with the catalysts described herein may also be used as catalysts for a variety of chemical reactions. The specific pore sizes of the LTA frameworks make them particularly suited for their use in catalyzing reactions including carbonylating DME with CO at low temperatures, reducing NOx with methane (e.g., in exhaust applications), cracking, dehydrogenating, converting paraffins to aromatics, MTO, isomerizing xylenes, disproportionating toluene, alkylating aromatic hydrocarbons, oligomerizing alkenes, aminating lower alcohols, separating and sorbing lower alkanes, hydrocracking a hydrocarbon, dewaxing a hydrocarbon feedstock, isomerizing an olefin, producing a higher molecular weight hydrocarbon from lower molecular weight hydrocarbon, reforming a hydrocarbon, converting a lower alcohol or other oxygenated hydrocarbon to produce an olefin products, epoxiding olefins with hydrogen peroxide, reducing the content of an oxide of nitrogen contained in a gas stream in the presence of oxygen, or separating nitrogen from a nitrogen-containing gas mixture by contacting the respective feedstock with the a catalyst comprising the crystalline microporous solid of any one of the silicate (including the pure-silicates, aluminosilicates, germanosilicates, and titanosilicates) under conditions sufficient to affect the named transformation.

The aluminosilicate solids appear to be especially suitable for converting a lower alcohols or other oxygenated hydrocarbon into olefin products by contacting the corresponding feedstock with a catalyst comprising a crystalline microporous aluminosilicates described herein, under conditions sufficient to affect the named transformation. Transformations of feedstocks comprising methanol are particularly facile.

Crystalline microporous titanosilicates having LTA topology are also useful as a catalyst for epoxiding olefins with hydrogen peroxide, by contacting the olefin with the a catalyst comprising a crystalline microporous titanosilicate solids, as described herein, under conditions sufficient to epoxide the olefin. In particularly useful embodiments, the olefin is an allylic alcohol.

Specific conditions for many of these transformations are known to those of ordinary skill in the art. Exemplary conditions for such reactions/transformations may also be found in WO/1999/008961, and U.S. Pat. No. 4,544,538, both of which are incorporated by reference herein in its entirety for all purposes.

Depending upon the type of reaction which is catalyzed, the microporous solid may be predominantly in the hydrogen form, partially acidic or substantially free of acidity. As used herein, "predominantly in the hydrogen form" means that, after calcination (which may also include exchange of the pre-calcined material with $NH_4^+$ prior to calcination), at least 80% of the cation sites are occupied by hydrogen ions and/or rare earth ions.

Use of the Inventive Compositions—Other

Molecular sieves with LTA topology, such as described herein, are also useful in other applications including removal of $H_2O$, $CO_2$ and $SO_2$ from fluid streams, such as low-grade natural gas streams, and separations of gases, including noble gases, $N_2$, $O_2$, fluorochemicals and formaldehyde). Exemplary applications will be apparent to the skilled person upon a reading of the present disclosure.

These LTA compositions may also be incorporated into polymer-composite membranes by known methods, the polymers comprising, for example, polyimide, polyethersulfone, polyetheretherketone, and mixtures and copolymers thereof. In other embodiments, the LTA compositions, as supported films or membranes, may be used as reaction templates, separation media, or dielectrics.

The following listing of embodiments is intended to complement, rather than displace or supersede, any of the previous descriptions.

Embodiment 1

A process for comprising hydrothermally treating an aqueous composition comprising:
(a) a source of a silicon oxide;
(b) an optional source of aluminum oxide;
(c) an optional source of germanium oxide;
(d) an optional source of titanium oxide;
(e) an optional source of one or more of boron oxide, gallium oxide, hafnium oxide, iron oxide, tin oxide, titanium oxide, indium oxide, vanadium oxide, zinc oxide, zirconium oxide, or combination or mixture thereof;
(f) a mineralizing agent; and
(g) an organic structure directing agent (OSDA) comprising a substituted benzyl-3H-imidazol-1-ium cation of Formula (I):

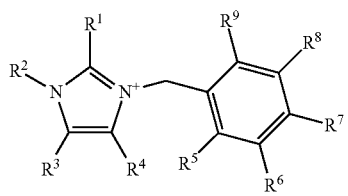

(I)

under conditions effective to crystallize a crystalline microporous solid of LTA topology;
wherein
$R^1$, $R^2$, and $R^7$ are independently $C_{1-3}$ alkyl;
$R^3$, $R^4$, $R^5$, $R^6$, $R^8$, and $R^9$ are independently H or $C_{1-3}$ alkyl.

In some Aspects of this Embodiment, the substituted benzyl-3H-imidazol-1-ium cation has an associated bromide, chloride, fluoride, iodide, nitrate, hydroxide, or other anion, preferably hydroxide. Other independent Aspects of this Embodiment provide for the absence of presence of any one or more sources of one or more of the optional metals or metalloids. Still other Aspects of this Embodiment include those where $R^1$, $R^2$, $R^3$, $R^4$, $R^5$, $R^6$, $R^7$, $R^8$, and $R^9$ are defined elsewhere herein.

In some Aspects of this Embodiment, the substituted benzyl-3H-imidazol-1-ium cation can be used in conjunction with lesser amounts of other OSDAs known to provide LTA topologies. These materials and their relative proportions are described elsewhere herein.

Embodiment 2

The process of Embodiment 1, wherein the OSDA comprises a 2,3-dialkyl-1-(4-alkyl-benzyl)-3H-imidazol-1-ium cation of Formula (IA):

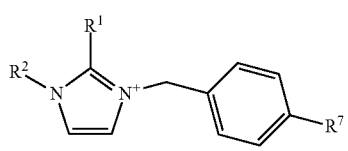

(IA)

Embodiment 3

The process of Embodiment 1, wherein the OSDA comprises a 2,3-dimethyl-1-(4-methyl-benzyl)-3H-imidazol-1-ium cation of Formula (IB):

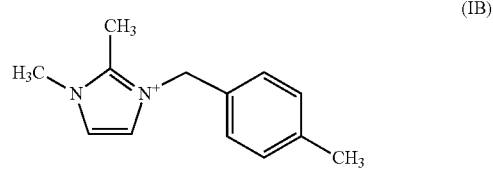

(IB)

2,3-Dimethyl-1-(4-methyl-benzyl)-3H-imidazol-1-ium; chloride

Embodiment 4

The process of any one of Embodiments 1 to 3, wherein the aqueous composition further comprises: (b) a source of an aluminum oxide. In independent Aspects of this Embodiment, the aqueous composition contains only sources of silicon and aluminum oxides, and in other Aspects, the aqueous composition contains any one or more of the optional source of the optional metal oxides.

Embodiment 5

The process of any one of Embodiments 1 to 5, wherein the aqueous composition further comprises: (c) a source of a germanium oxide. In independent Aspects of this Embodiment, the aqueous composition contains only sources of silicon and germanium oxides, and in other Aspects, the aqueous composition contains any one or more of the optional source of the optional metal oxides.

Embodiment 6

The process of any one of Embodiments 1 to 6, wherein the aqueous composition further comprises: (d) a source of a titanium oxide. In independent Aspects of this Embodiment, the aqueous composition contains only sources of silicon and titanium oxides, and in other Aspects, the aqueous composition contains any one or more of the optional source of the optional metal oxides.

Embodiment 7

The process of any one of Embodiments 1 to 3, wherein the hydrothermal treatment provides a crystalline microporous silicate solid of LTA topology. In one Aspect of this Embodiment, the crystalline microporous solid of LTA topology is a pure silicate, the term "pure" reflecting the absence of all but the inevitable impurities present in the sources of silicon oxide.

Embodiment 8

The process of Embodiment 4, wherein the hydrothermal treatment provides a crystalline microporous aluminosilicate solid of LTA topology. In one Aspect of this Embodiment, the crystalline microporous solid of LTA topology is a pure aluminosilicate, the term "pure" reflecting the absence of all but the inevitable impurities present in the sources of aluminum and silicon oxides

Embodiment 9

The process of Embodiment 5, wherein the hydrothermal treatment provides a crystalline microporous germanosilicate solid of LTA topology. In one Aspect of this Embodiment, the crystalline microporous solid of LTA topology is a pure germanosilicate, the term "pure" reflecting the absence of all but the inevitable impurities present in the sources of germanium and silicon oxides.

Embodiment 10

The process of Embodiment 6, wherein the hydrothermal treatment provides a crystalline microporous titanosilicate solid of LTA topology. In one Aspect of this Embodiment, the crystalline microporous solid of LTA topology is a pure titanosilicate, the term "pure" reflecting the absence of all but the inevitable impurities present in the sources of silicon and titanium oxides.

Embodiment 11

The process of any one of Embodiments 1 to 10, wherein the OSDA cation has an associated fluoride or hydroxide ion preferably substantially free of other halide counterions. In separate Aspects of this Embodiment, the associated anion is hydroxide.

Embodiment 12

The process of any one of Embodiments 1 to 11, wherein:
(a) the source of silicon oxide comprises an alkoxide, a silicate, silica hydrogel, silicic acid, fumed silica, colloidal silica, tetra-alkyl orthosilicate, a silica hydroxide, a silicon alkoxide, or combination thereof;
(b) the source of aluminum oxide, when present, comprises an alkoxide, hydroxide, or oxide of aluminum, a sodium aluminate, or combination thereof;
(c) the source of germanium oxide, when present, comprises a alkali metal orthogermanate, $M_4GeO_4$, containing discrete $GeO_4^{4-}$ ions, $GeO(OH)_3^-$, $GeO_2(OH)_2^{2-}$, $[(Ge(OH)_4)_8(OH)_3]^{3-}$ or neutral solutions of germanium dioxide containing $Ge(OH)_4$, or an alkoxide or carboxylate derivative thereof;
(d) the source of titanium oxide, when present, comprises a titanium alkoxide, oxide, or hydroxy oxide; and
(e) the source of boron oxide, gallium oxide, hafnium oxide, iron oxide, tin oxide, titanium oxide, indium oxide, vanadium oxide, zinc oxide, zirconium oxide.

Embodiment 13

The process of any one of Embodiments 1 to 12, wherein the mineralizing agent is or comprises an aqueous hydroxide.

Embodiment 14

The process of any one of Embodiments 1 to 12, wherein the mineralizing agent is or comprises hydrofluoric acid (HF). In different aspects of this Embodiment, the HF is added as such or generated in situ using fluoride sources in the presence of strong acids.

Embodiment 15

The process of any one of Embodiments 1 to 14, wherein:
(a) the molar ratio of the OSDA:Si is in a range of from 0.1 to 1, preferably in a range of from 0.4 to 0.6;
(b) the molar ratio of Al:Si is in a range of from 0 to 0.1 or 0.005 to 0.1 (or Al is absent or Si/Al=10 to 200)
(c) the molar ratio of Ge:Si is in a range of from 0 to 1 or 0.05 to 1 (or Ge is absent or Si/Ge=1 to infinity or 1 to 20); or
(d) the molar ratio of Ti:Si is in a range of from 0 to 0.1 or 0.01 to 0.1 (or Si/Ge=1 to infinity or 1 to 20).

Embodiment 16

The process of any one of Embodiments 1 to 15, wherein:
(e) the molar ratio of water:Si is in a range of from about 2 to about 50, preferably in a range of from about 4 to about 10.

Embodiment 17

The process of any one of Embodiments 1 to 16, wherein:
(f) the molar ratio of OSDA:Si is in a range of from about 0.1 to about 0.75, preferably in a range of from about 0.4 to about 0.6.

Embodiment 18

The process of any one of Embodiments 1 to 17, wherein the mineralizing agent is HF and:
(g) the molar ratio of fluoride:Si is in a range of from about 0.1 to about 0.75, preferably in a range of from about 0.4 to about 0.6.

Embodiment 19

The process of any one of Embodiments 1 to 18, wherein the conditions effective to crystallize a crystalline microporous LTA topology include treatment of the respective hydrothermally treated aqueous composition at a temperature in a range of from 100° C. to 200° C. In certain Aspects of this Embodiment, the temperature is in a range of from, 120° C. to 160° C., for a time effective for crystallizing the crystalline microporous solid of LTA topology. In certain Aspects of this Embodiment, the times and temperatures include ranges described elsewhere herein.

Embodiment 20

The process of any one of Embodiments 1 to 19, wherein the conditions effective to crystallize a crystalline microporous LTA topology include treatment of the respective hydrothermally treated aqueous composition at a temperature in a range of from 100° C. to 200° C. for a time in a range of from 3 to 40 days, preferably from 7 to 40 days.

Embodiment 21

The process of any one of Embodiments 1 to 20, further comprising isolating the crystalline microporous solid of LTA topology.

Embodiment 22

The process of Embodiment 21, wherein the isolated the crystalline microporous solid of LTA topology is a pure silicate, an aluminosilicate, a germanosilicate, or a titanosilicate. In other Aspects of this embodiment, the isolated microcrystalline is described as a silicate or heteratom-substituted silicate, as defined herein.

Embodiment 23

The process of Embodiment 21 or 22, further comprising:
(a) heating the isolated crystalline microporous solid at a temperature in a range of from about 250° C. to about 450° C.;
(b) contacting the isolated crystalline microporous solid with ozone or other oxidizing agent at a temperature in a range of 100° C. to 200° C.;
or
(c) heating the isolated crystalline microporous solid at a temperature in a range of from about 200° C. to about 600° C. in the presence of an alkali, alkaline earth, transition metal, rare earth metal, ammonium or alkylammonium salt;
for a time sufficient to form a dehydrated or an OSDA-depleted product.

Embodiment 24

The process of Embodiment 23, further comprising:
(a) treating the dehydrated or OSDA-depleted product with an aqueous alkali, alkaline earth, transition metal, rare earth metal, ammonium or alkylammonium salt, as described elsewhere herein; and/or
(b) treating the dehydrated or OSDA-depleted product with at least one type of transition metal or transition metal oxide, as described elsewhere herein.

Embodiment 25

A composition prepared by a process of Embodiment 21 or 22. In one Aspect of this Embodiment, the composition comprises a plurality of loose crystalline microporous solid. In another Aspect of this Embodiment, the composition comprises a film or membrane of the named composition.

Embodiment 26

A composition prepared by the process of Embodiment 23.

Embodiment 27

A composition prepared by the process of Embodiment 24.

Embodiment 28

A composition comprising:
(a) a source of a silicon oxide;
(b) an optional source of aluminum oxide;
(c) an optional source of germanium oxide;
(d) an optional source of titanium oxide;
(e) an optional source of one or more of boron oxide, gallium oxide, hafnium oxide, iron oxide, tin oxide, titanium oxide, indium oxide, vanadium oxide, zinc oxide, zirconium oxide, or combination or mixture thereof;
(f) a mineralizing agent; and
(g) an organic structure directing agent (OSDA) comprising a substituted benzyl-3H-imidazol-1-ium cation of Formula (I):

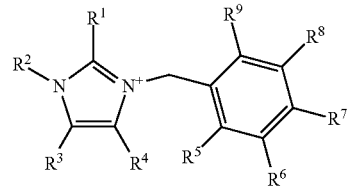

and
(h) a compositionally consistent crystalline microporous silicate solid of LTA topology;
wherein
$R^1$, $R^2$, and $R^7$ are independently $C_{1-6}$ alkyl, preferably $C_{1-3}$ alkyl;
$R^3$, $R^4$, $R^5$, $R^6$, $R^8$, and $R^9$ are independently H or $C_{1-3}$ alkyl; and the substituted benzyl-3H-imidazol-1-ium cation has an associated bromide, chloride, fluoride, iodide, nitrate, or hydroxide anion. Independent Aspects of this Embodiment include those compositions in which the sources and ratios of the source or optional sources of metal oxides are as describe elsewhere herein.

Embodiment 29

The composition of Embodiment 28, wherein the OSDA comprises a 2,3-dialkyl-1-(4-alkyl-benzyl)-3H-imidazol-1-ium cation of Formula (IA):

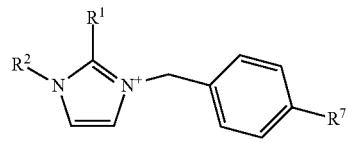

Embodiment 30

The composition of Embodiment 28, wherein the OSDA comprises a 2,3-dimethyl-1-(4-methyl-benzyl)-3H-imidazol-1-ium cation of Formula (IB):

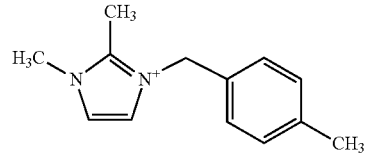

Embodiment 31

The composition of any one of Embodiments 28 to 30, wherein the aqueous composition further comprises:
(b) a source of an aluminum oxide; and
(h) a compositionally consistent crystalline microporous aluminosilicate solid of LTA topology.

Embodiment 32

The composition of any one of Embodiments 28 to 31, wherein the aqueous composition further comprises:
(c) a source of a germanium oxide; and
(h) a compositionally consistent crystalline microporous germanosilicate solid of LTA topology.

Embodiment 33

The composition of any one of Embodiments 28 to 32, wherein the aqueous composition further comprises:
(d) a source of a titanium oxide; and
(h) a compositionally consistent crystalline microporous titanosilicate solid of LTA topology.

Embodiment 34

The composition of any one of Embodiments 28 to 33, wherein the mineralizing agent is or comprises an aqueous hydroxide, for example an aqueous alkali metal or alkaline earth metal hydroxide.

Embodiment 35

The composition of any one of Embodiments 28 to 33, wherein the mineralizing agent is or comprises hydrofluoric acid (HF).

Embodiment 36

The composition of any one of claims 17-22, wherein:
(a) the molar ratio of OSDA:Si is in a range of from 0.1 to 1, preferably in a range of from 0.6 to 0.6;
(b) the molar ratio of Al:Si is in a range of from 0 to 0.1 or 0.005 to 0.1 (or Al is absent or Si/Al=10 to 200)
(c) the molar ratio of Ge:Si is in a range of from 0 to 1 or 0.05 to 1 (or Ge is absent or Si/Ge=1 to infinity or 1 to 20); or
(d) the molar ratio of Ti:Si is in a range of from 0 to 0.1 or 0.01 to 0.1 (or Si/Ge=1 to infinity or 1 to 20).

Embodiment 37

The composition of any one of Embodiments 28 to 36, wherein:
(e) the molar ratio of water:Si is in a range of from about 2 to about 50, preferably in a range of from about 4 to about 10.

Embodiment 38

The composition of any one of Embodiments 28 to 37, wherein:
(f) the molar ratio of OSDA:Si is in a range of from about 0.1 to about 0.75, preferably in a range of from about 0.4 to about 0.6.

Embodiment 39

The composition of any one of Embodiments 28 to 38, wherein the mineralizing agent is HF and:
(g) the molar ratio of fluoride:Si is in a range of from about 0.1 to about 0.75, preferably in a range of from about 0.4 to about 0.6.

Embodiment 40

The composition of any one of Embodiments 28 to 39, that is present at a temperature in a range of from 100° C. to 200° C., preferably from 125° C. to 160° C.

Embodiment 41

The composition of any one of Embodiments 28 to 40 that is a suspension or a gel.

Embodiment 42

A crystalline microporous silicate solid of LTA topology containing within its pores an OSDA comprising substituted benzyl-3H-imidazol-1-ium cation of Formula (I):

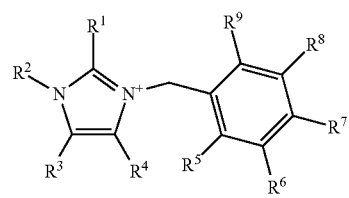

wherein
$R^1$, $R^2$, and $R^7$ are independently $C_{1-6}$ alkyl, preferably $C_{1-3}$ alkyl; and
$R^3$, $R^4$, $R^5$, $R^6$, $R^8$, and $R^9$ are independently H or $C_{1-3}$ alkyl.

Embodiment 43

A crystalline microporous aluminosilicate solid of LTA topology containing within its pores an OSDA comprising a substituted benzyl-3H-imidazol-1-ium cation of Formula (I):

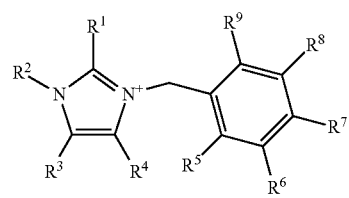

wherein
$R^1$, $R^2$, and $R^7$ are independently $C_{1-6}$ alkyl, preferably $C_{1-3}$ alkyl; and
$R^3$, $R^4$, $R^5$, $R^6$, $R^8$, and $R^9$ are independently H or $C_{1-3}$ alkyl.

Embodiment 44

A crystalline microporous germanosilicate solid of LTA topology containing within its pores an OSDA comprising a substituted benzyl-3H-imidazol-1-ium cation of Formula (I):

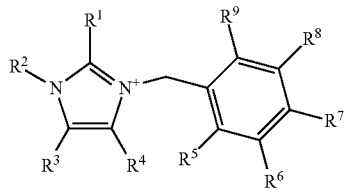

(I)

wherein

R$^1$, R$^2$, and R$^7$ are independently C$_{1-6}$ alkyl, preferably C$_{1-3}$ alkyl; and R$^3$, R$^4$, R$^5$, R$^6$, R$^8$, and R$^9$ are independently H or C$_{1-3}$ alkyl. Other Aspects of this Embodiment, with respect to the definitions of R$^1$, R$^2$, R$^3$, R$^4$, R$^5$, R$^6$, R$^7$, R$^8$, and R$^9$ are described herein.

Embodiment 45

A crystalline microporous titanosilicate solid of LTA topology containing within its pores an OSDA comprising a substituted benzyl-3H-imidazol-1-ium cation of Formula (I):

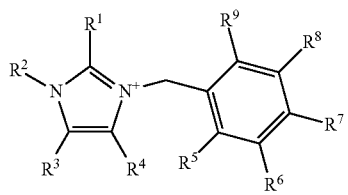

(I)

wherein

R$^1$, R$^2$, and R$^7$ are independently C$_{1-6}$ alkyl, preferably C$_{1-3}$ alkyl; and R$^3$, R$^4$, R$^5$, R$^6$, R$^8$, and R$^9$ are independently H or C$_{1-3}$ alkyl.

Embodiment 46

The crystalline microporous solid of LTA topology of any one of Embodiments 42 to 45, wherein the OSDA comprises a 2,3-dialkyl-1-(4-alkyl-benzyl)-3H-imidazol-1-ium cation of Formula (IA):

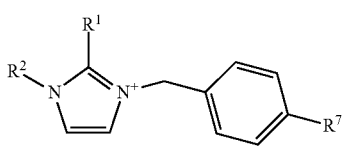

(IA)

Embodiment 47

The crystalline microporous solid of LTA topology of any one of Embodiments 42 to 46, wherein the OSDA comprises a 2,3-dimethyl-1-(4-methyl-benzyl)-3H-imidazol-1-ium cation of Formula (IB):

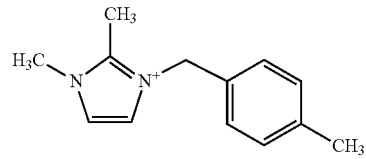

(IB)

Embodiment 48

The crystalline microporous solid of LTA of Embodiments 42 to 47, further containing within its pores fluoride ion.

Embodiment 49

A crystalline microporous pure-silicate, aluminosilicate, germanosilicate, or titanosilicate solid of LTA topology, prepared by any of the processes described herein, that is substantially free of an Organic Structure Directing Agent (OSDA). In certain Aspects of this Embodiment, the aluminosilicates product has a molar ratio of Si:Al in a range of from about 5 to 6, from 6 to 8, from 8 to 10, from 10 to 14, from 14 to 18, from 18 to 22, from 22 to 26, from 26 to 30, from 30 to 34, from 34 to 38, from 38 to 42, from 42 to 44, from 44 to 46, from 46 to 50, or a range combining any two or more of these ranges, for example, from 12 to 42

Embodiment 50

The crystalline microporous pure-silicate, aluminosilicate, germanosilicate, or titanosilicate solid of LTA topology of Embodiment 49, comprising pores, at least some of which contain Li, Na, K, Rb, Cs, Be, Mg, Ca, Sr, Be, Al, Ga, In, Zn, Ag, Cd, Ru, Rh, Pd, Pt, Au, Hg, La, Ce, Pr, Nd, Pm, Sm, Eu, or R$_{4-n}$N$^+$H$_n$ cations, where R is alkyl, n=0–4. In specific Aspects of this Embodiment, the pores contain NaCl or KCl.

Embodiment 51

The crystalline microporous solid of Embodiment 49 or 50, comprising pores, at least some of which contain scandium, yttrium, titanium, zirconium, vanadium, manganese, chromium, molybdenum, tungsten, iron, ruthenium, osmium, cobalt, rhodium, iridium, nickel, palladium, platinum, copper, silver, gold, or a mixture thereof, each as a metal, oxide, or salt. In one Aspect of this Embodiment, the pores contain copper, as metal, oxide, or salt.

Embodiment 52

Figure 14B:
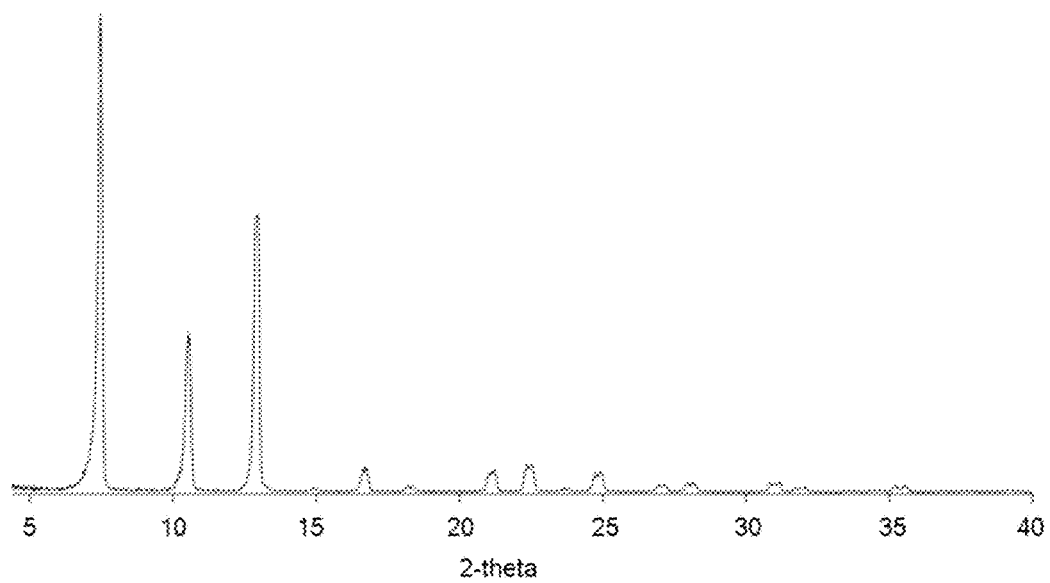

The crystalline microporous silicate, aluminosilicate, germanosilicate, or titanosilicate solid of LTA topology of any one of Embodiments 49 to 51, the solid exhibiting one or more one of the following characteristics:

(a) an XRD pattern having at least the five major peaks substantially as provided in Table 2A or 2B;

(b) an XRD diffraction pattern the same as or consistent with any one of those shown in FIG. 5, FIG. 12, or FIG. 14(A or B);

(c) unit cell substantially the same as those shown in any one of Tables 3-5;

(d) an $^{29}$Si MAS spectrum the same as or consistent with either of those shown in FIG. 7(A) or (B);

(e) an $^{27}$Al MAS spectrum the same as or consistent with either of those shown in FIG. 13(A) or (B); and (f) an physisorption isotherm with $N_2$-gas or with argon the same as or consistent with any one of those shown in FIG. 7 (A-C).

Embodiment 53

A process comprising carbonylating DME with CO at low temperatures, reducing NOx with methane, cracking, dehydrogenating, converting paraffins to aromatics, MTO, isomerizing xylenes, disproportionating toluene, alkylating aromatic hydrocarbons, oligomerizing alkenes, aminating lower alcohols, separating and sorbing lower alkanes, hydrocracking a hydrocarbon, dewaxing a hydrocarbon feedstock, isomerizing an olefin, producing a higher molecular weight hydrocarbon from lower molecular weight hydrocarbon, reforming a hydrocarbon, converting a lower alcohol or other oxygenated hydrocarbon to produce an olefin products, epoxiding olefins with hydrogen peroxide, reducing the content of an oxide of nitrogen contained in a gas stream in the presence of oxygen, or separating nitrogen from a nitrogen-containing gas mixture by contacting the respective feedstock with the a catalyst comprising the crystalline microporous solid of any one of Embodiments 49 to 52 under conditions sufficient to affect the named transformation.

Embodiment 54

The process of Embodiment 53, comprising converting a lower alcohol or other oxygenated hydrocarbon to produce an olefin products by contacting the respective feedstock with the a catalyst comprising any one of the crystalline microporous aluminosilicate solids of Embodiments 49 to 52 under conditions sufficient to affect the named transformation.

Embodiment 55

The process of Embodiment 53, wherein the lower alcohol or other oxygenated hydrocarbon is methanol.

Embodiment 56

The process of Embodiment 53, comprising epoxiding an olefin with hydrogen peroxide, by contacting the olefin with the a catalyst comprising any one of the crystalline microporous titanosilicate solids of Embodiments 49 to 52 under conditions sufficient to epoxide the olefin.

Embodiment 57

The process of Embodiment 56, wherein the olefin is an allylic alcohol.

Embodiment 58

A process comprising removing of $H_2O$, $CO_2$ and $SO_2$ from fluid streams, such as low-grade natural gas streams, and separating gases, including noble gases, $N_2$, $O_2$, fluorochemicals and formaldehyde, from gas streams.

EXAMPLES

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees Celsius, pressure is at or near atmospheric.

Example 1. Materials and Methods

Unless otherwise noted, all reagents were purchased from commercial sources and were used as received. Unless otherwise noted all, reactions were conducted in flame-dried glassware under an atmosphere of argon. Hydroxide ion exchanges were performed using Supelco Dowex Monosphere 550A UPW hydroxide exchange resin with an exchange capacity of 1.1 meq/mL. Titrations were performed using a Mettler-Toledo DL22 autotitrator using 0.01 M HCl as the titrant. All liquid NMR spectra were recorded with a 400 MHz Varian Spectrometer. Liquid NMR spectra were recorded on Varian Mercury spectrometers.

All powder x-ray diffraction characterization were conducted on a Rigaku MiniFlex II diffractometer with Cu Kα radiation.

Solid-state NMR ($^{13}$C, $^{19}$F, $^{27}$Al and $^{29}$Si) spectra were obtained using a Bruker DSX-500 spectrometer (11.7 T) and a Bruker 4 mm MAS probe. The spectral operating frequencies were 500.2 MHz, 125.721 MHz, 470.7 MHz, 130.287 MHz and 99.325 MHz for $^1$H, $^{13}$C, $^{19}$F, $^{27}$Al and $^{29}$Si nuclei, respectively. Spectra were referenced to external standards as follows: tetramethylsilane (TMS) for $^1$H and $^{29}$Si, adamantane for $^{13}$C as a secondary external standard relative to tetramethylsilane, CFCl$_3$ for $^{19}$F and 1.0 M Al(NO$_3$)$_3$ aqueous solution for $^{27}$Al. Samples were spun at 14 kHz for 1H and $^{27}$Al MAS NMR and 8 kHz for $^{13}$C and $^{29}$Si MAS and CPMAS NMR experiments. $^{19}$F MAS NMR spectra were collected at both 13 and 15 kHz to assign spinning side bands. For detection of the $^{27}$Al signal, a short 0.5 μs-/18 pulse was used before FID was recorded in order to make quantitative comparison among resonances.

Thermogravimetric analysis (TGA) was performed on a Perkin Elmer STA 6000 with a ramp of 10° C.min$^{-1}$ to 900° C. under air atmosphere. Samples (0.01-0.06 g) were placed in aluminum crucible and heated at 1 K/min in a flowing stream (0.667 cm$^3$/s) comprised of 50% air (Air Liquide, breathing grade) and 50% argon (Air Liquide, UHP).

SEM analyses were performed on a ZEISS 1550 VP FESEM, equipped with an Oxford X-Max SDD X-ray Energy Dispersive Spectrometer (EDS) system for determining the Si/Al ratios of the samples.

Example 2. Synthesis of 1,2-dimethyl-3-(4-methylbenzyl)-1H-imidazol-3-ium Hydroxide The 1,2-dimethyl-3-(4-methylbenzyl)-1H-imidazol-3-ium hydroxide was synthesized according to the scheme shown in FIG. 3. A 500 mL flask was charged with 1,2-dimethyl imidazole (11.60 grams, 121.0 mmols), 4-methylbenzyl chloride (15.46 grams, 110.0 mmols) and toluene (125 mL). The flask was fitted with a reflux condenser and heated to reflux for 15 hours. The reaction was cooled to 25° C. and resulting solids were filtered and washed with ethyl acetate (3×50 mL) to give the OSDA (24.10 grams, 92% yield) as a white solid. $^1$H NMR (500 MHz, CD$_3$OD): δ 7.54-7.53 (m, 2H), 7.28 (d, J=5.0, 2H), 7.28 (d, J=5.0, 2H), 5.34 (s, 2H), 3.87 (s, 3H), 2.67 (s, 3H), 2.39 (s, 3H). $^{13}$C NMR (126 MHz, CD3OD) δ 144.8, 138.8, 130.7, 129.5, 127.6, 122.4, 121.1, 51.2, 34.1, 19.7, 8.4.

The OSDA was then converted to hydroxide form using hydroxide exchange resin (Dowex Marathon A, hydroxide form) in water, and the product was titrated using a Mettler-Toledo DL22 autotitrator using 0.01 M HCl as the titrant.

Example 3. Syntheses of Molecular Sieves

Example 3.1. General Synthetic Methods (FIG. 2)

A general synthesis procedure for fluoride syntheses was as follows. Tetraethylorthosilicate (TEOS), tetramethylammonium hydroxide (if necessary) and aluminopropoxide (if necessary) were added to the organic in its hydroxide form. The container was closed and stirred for at least 12 hours to allow for complete hydrolysis. The lid was then removed and the ethanol and appropriate amount of water were allowed to evaporate under a stream of air. It was assumed that all the ethanol evaporated along with the water. Once the appropriate mass was reached the material was transferred to a Teflon Parr Reactor and aqueous HF was added and the mixture was hand-stirred until a homogenous gel was obtained. If desired, seeds were added at this point. The autoclave was sealed and placed in a rotating oven at temperatures ranging from 140 to 175° C. Aliquots of the material were taken periodically by first quenching the reactor in water and then removing enough material for powder x-ray diffraction (PXRD).

Example 3.1. Synthesis of Germanosilicates

All reactions were performed in 23 mL Teflon-lined stainless steel autoclaves (Parr instruments). Reactions were performed statically or tumbled at 43 rpm using spits built into convection ovens. Syntheses were performed at 125, 140, 150, 160, or 175° C. Silicon source was tetraethyl orthosilicate (TEOS, 99.9% Si(OCH$_2$CH$_3$)$_4$, Strem). Germanium source was germanium oxide (99.99% GeO$_2$, Strem).

Gels for the germanosilicate reactions were prepared by adding germanium oxide to a solution of OSDA in water directly in the 23 mL Teflon liner. This mixture was stirred at 25° C. for 5 minutes, or until the germanium oxide dissolved into the solution. TEOS was then added, the reaction vessel was capped, and stirred for an additional 12 hours to hydrolyze the TEOS. The reaction vessel was then uncapped and a stream of air was blown over the gel while it was mechanically stirred until the appropriate excess of water and hydrolyzed ethanol had been evaporated. In certain cases, the gel was put under vacuum to remove small amounts of residual water, when evaporation failed to remove the appropriate amount of water. Hydrofluoric acid was then added in a drop wise fashion to the gel, the gel was quickly stirred with a Teflon spatula, and the Teflon liner was sealed into the stainless steel autoclave and put into the oven. The reactors were opened every 6-7 days to assess reaction progress. After homogenizing, a small sample was successively washed with D.I. H$_2$O (2×10 mL) and acetone:methanol (1:1, 3×10 mL). The PXRD pattern of the resulting product was inspected. All reactions were monitored for at least 1 month or until a crystalline product was observed.

Example 3.2. Synthesis of Pure-Silica LTA

Pure-silica materials were prepared in the same manner as germanosilicate materials except that the addition of GeO$_2$ was omitted.

Example 3.2. Synthesis of Aluminosilicate LTA

Aluminosilicate materials were prepared in the same manner as germanosilicate materials except that the addition of GeO$_2$ was omitted and aluminum isopropoxide was used as the aluminum source (99.9% Al(O-iPr)$_3$, Sigma Aldrich).

Example 3.2. Synthesis of Synthesis of Titanosilicate LTA

Titanosilicate materials were prepared in the same manner as germanosilicate materials except that the addition of GeO$_2$ was omitted and titanium(IV) butoxide was used as the titanium source.

The synthetic parameters used to make these LTA materials and the resulting materials are described in Table 1.

TABLE 1

Synthesis results. In each case, the molar ratio of H$_2$O/Si was 5 and the molar ratio of HF/Si was 0.5. TMA is tetramethylammonium hydroxide. The OSDA was 2,3-dimethyl-1-(4-methyl-benzyl)-3H-imidazol-1-ium hydroxide.

| Ref. # | Gel Ratios | | | | | Conditions | | | | Si/Al Product ratio |
|---|---|---|---|---|---|---|---|---|---|---|
| | Si/Al | Si/Ge | Si/Ti | TMA/Si | OSDA/Si | Seeds | Temp. | Days | Result | |
| 1 | — | 2 | — | — | 0.5 | — | 160° C. | 14 | BEC | |
| 2 | — | 4 | — | — | 0.5 | — | 160° C. | 14 | BEC | |
| 3 | — | 8 | — | — | 0.5 | — | 160° C. | 14 | LTA | |
| 4 | — | 16 | — | — | 0.5 | — | 160° C. | 14 | LTA/BEA | |
| 5 | — | 16 | — | — | 0.5 | — | 140° C. | 14 | LTA | |
| 6 | ∞ | — | — | 0.05 | 0.45 | — | 125° C. | 7 | LTA | — |
| 7 | ∞ | — | — | 0.05 | 0.45 | Silica LTA | 125° C. | 7 | LTA | — |
| 8 | ∞ | — | — | — | 0.5 | Silica LTA | 125° C. | 14 | LTA | — |
| 9 | ∞ | — | — | — | 0.5 | — | 160° C. | 14 | LTA | — |
| 10 | ∞ | — | — | — | 0.5 | — | 160° C. | 40 | None | — |
| 11 | ∞ | — | — | — | 0.5 | — | 140° C. | 40 | None | — |
| 12 | ∞ | — | — | 0.25 | 0.25 | — | 125° C. | 7 | AST | — |

TABLE 1-continued

Synthesis results. In each case, the molar ratio of $H_2O/Si$ was 5 and the molar ratio of HF/Si was 0.5. TMA is tetramethylammonium hydroxide. The OSDA was 2,3-dimethyl-1-(4-methyl-benzyl)-3H-imidazol-1-ium hydroxide.

| Ref. # | Gel Ratios | | | | | Conditions | | | Result | Si/Al Product ratio |
|---|---|---|---|---|---|---|---|---|---|---|
| | Si/Al | Si/Ge | Si/Ti | TMA/Si | OSDA/Si | Seeds | Temp., | Days | | |
| 13 | 20 | — | — | 0.05 | 0.45 | Silica LTA | 125° C. | 9 | LTA | 12 |
| 14 | 50 | — | — | 0.05 | 0.45 | Silica LTA | 125° C. | 7 | LTA | 33 |
| 15 | 75 | — | — | 0.05 | 0.45 | Silica LTA | 125° C. | 7 | LTA | 38 |
| 16 | 100 | — | — | 0.05 | 0.45 | Silica LTA | 125° C. | 7 | LTA | 42 |
| 17 | — | — | 100 | | | Silica LTA | 125° C. | | LTA | |

For these fluoride-mediated reactions, the total organic content was held constant for all syntheses. LTA was first identified as a product in the germanium-containing syntheses, perhaps not surprising, as germanium is known to favor the formation of double four rings [D4Rs] and the entire LTA structure can be formed from D4Rs. Additionally, it was found that the formation of LTA was favored at lower temperatures, as BEC formed instead at higher temperatures even in germanosilicate systems.

The synthesis of pure-silica LTA was favored by either seeding the syntheses or by adding a small amount of tetramethyl ammonium hydroxide (TMAOH) (see Table 1). The addition of TMAOH helped form pure-silica LTA, but it was added in small amounts to avoid the formation of AST. Additionally, the use of seeds at lower synthesis temperatures helped to avoid the formation of competing phases. The water content was held constant for all syntheses, as the ratio used is easy to obtain in these types of reactions.

Using this new OSDA, the synthesis of ITQ-29 is much simpler than previously reported, as the new methodology has a much higher water content and a lower amount of TMA, avoiding the competing formation of AST.

Example 4. Characterizations of Products

Example 4.1. Pure-Silicate Materials

Example 4.1.1. Scanning Electron Microscopy (SEM) and Energy-Dispersive X-Ray spectroscopy (EDS)

Figure 4:
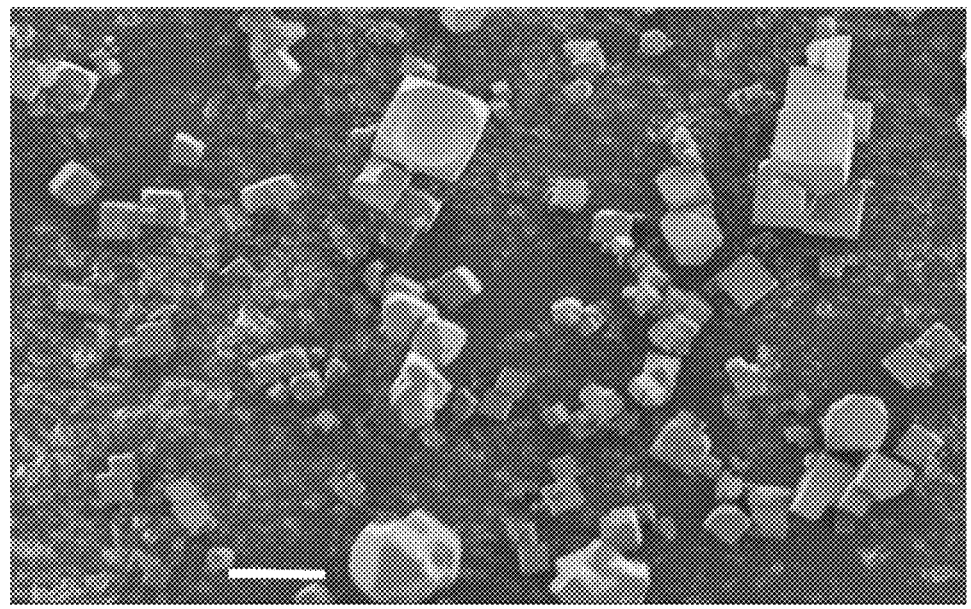
FIG. 4 shows an SEM image of an exemplary pure-silica LTA. Bar=30 microns.

The morphology of a pure silicate material was studied using SEM and a representative micrograph is shown in FIG. 4.

Example 4.1.2. Powder X-ray Diffraction (PXRD) Analysis

Figure 6:
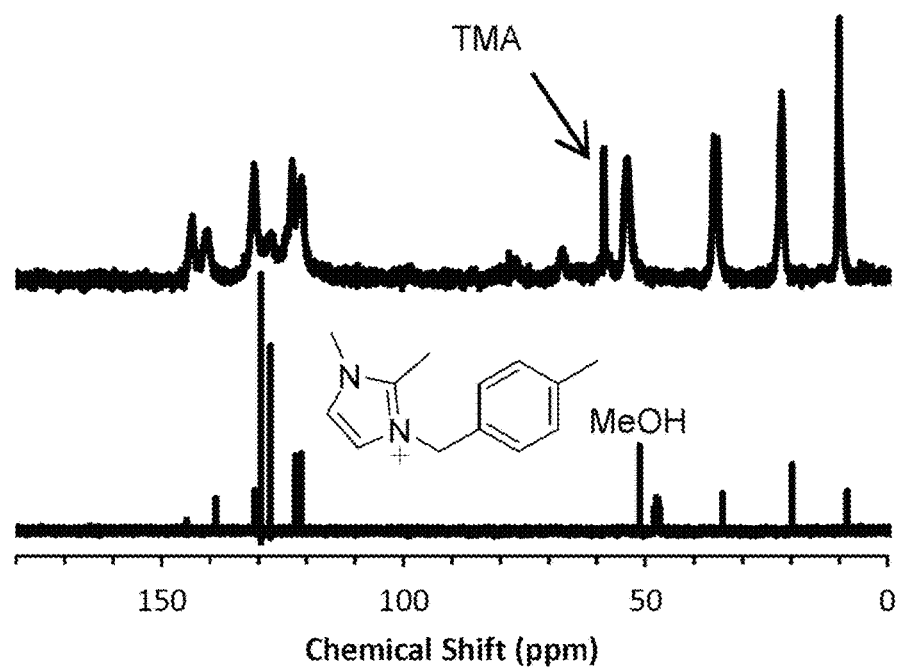
FIG. 6 shows the OSDA used to make pure-silica LTA along with the liquid carbon NMR (lower) and the $^{13}$C CPMAS NMR of as-made pure silica LTA. The relative sharpness of the TMA resonance (marked by arrow) is narrow due to its fast rotation within the pores.

Powder X-ray diffraction (PXRD) patterns of the as-made and calcined pure-silica LTA are shown in FIG. 5. It was confirmed by $^{13}C$ CP-MAS NMR that both the OSDA and TMA were occluded intact in the as-made material (FIG. 6). Tabulated PXRD data are provided in Tables 2A and 2B.

TABLE 2A

Tabulated PXRD data for a compositions of LTA topology. Relative intensities subject to variation. Values presented here for calcined materials.

| 2-theta | Relative Intensity |
|---|---|
| 7.3 ± 0.3 | 1000 |
| 10.4 ± 0.3 | 420 |
| 12.8 ± 0.3 | 330 |
| 16.6 ± 0.3 | 70 |
| 21.1 ± 0.3 | 80 |
| 22.4 ± 0.3 | 164 |
| 24.7 ± 0.3 | 80 |
| 28.0 ± 0.3 | 35 |
| 31.0 ± 0.3 | 40 |
| 31.9 ± 0.3 | 20 |

TABLE 2B

Tabulated PXRD data for a compositions of LTA topology. Relative intensities subject to variation. Values presented here for as-made materials.

| 2-theta | Relative Intensity |
|---|---|
| 7.6 ± 0.3 | 1000 |
| 10.6 ± 0.3 | 430 |
| 13.0 ± 0.3 | 940 |
| 15.1 ± 0.3 | 190 |
| 21.4 ± 0.3 | 210 |
| 22.7 ± 0.3 | 840 |
| 25.1 ± 0.3 | 280 |
| 27.3 ± 0.3 | 130 |
| 28.3 ± 0.3 | 190 |
| 31.3 ± 0.3 | 140 |

Example 4.1.3. Nuclear Magnetic Resonance

Figure 7B:
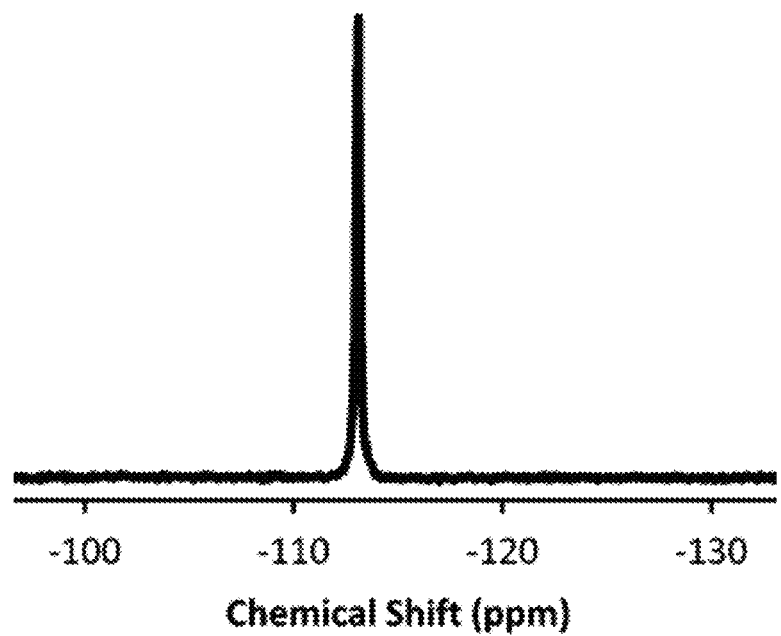

The $^{29}Si$ Bloch Decay NMR of the as-made (FIG. 7(A)) and calcined pure-silicate material (FIG. 7(B)) revealed a single resonance at −113.3 ppm, consistent with the single T-site in the LTA structure, and very few defects.

Figure 8:
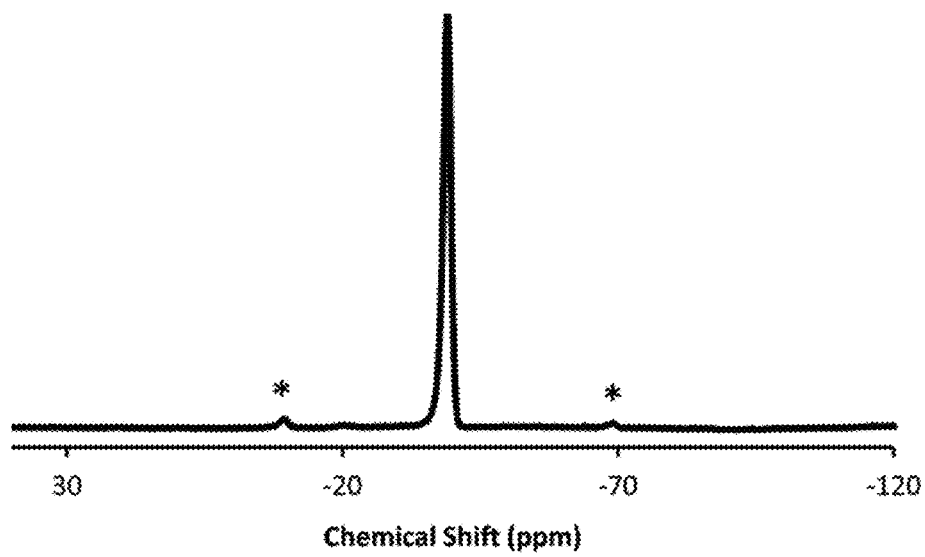
FIG. 8 shows an $^{19}$F NMR of as-made silica LTA. Spinning sidebands are marked with *.

The $^{19}F$ NMR of the as-made material ((FIG. 8) showed a single resonance at −39 ppm, consistent with the fluoride anion being occluded in the double four rings (D4Rs) of the LTA.

Example 4.1.4. Isotherm Data

The calcined material was characterized by argon and nitrogen adsorption isotherms obtained at −196° C. and −186° C. respectively, with a Quantachrome Autosorb iQ instrument. Prior to analysis, the samples were outgassed under vacuum at 200° C. The t-plot method was used to calculate the micropore volumes on the adsorption branch. The results shown in FIGS. 9(A-C) are consistent with the expected values. The argon adsorption isotherm shows a sharp, low-pressure transition, consistent with well-defined 8MRs.

Example 4.1.5. Computational Analysis for Pure-Silicate LTA

Figure 10:
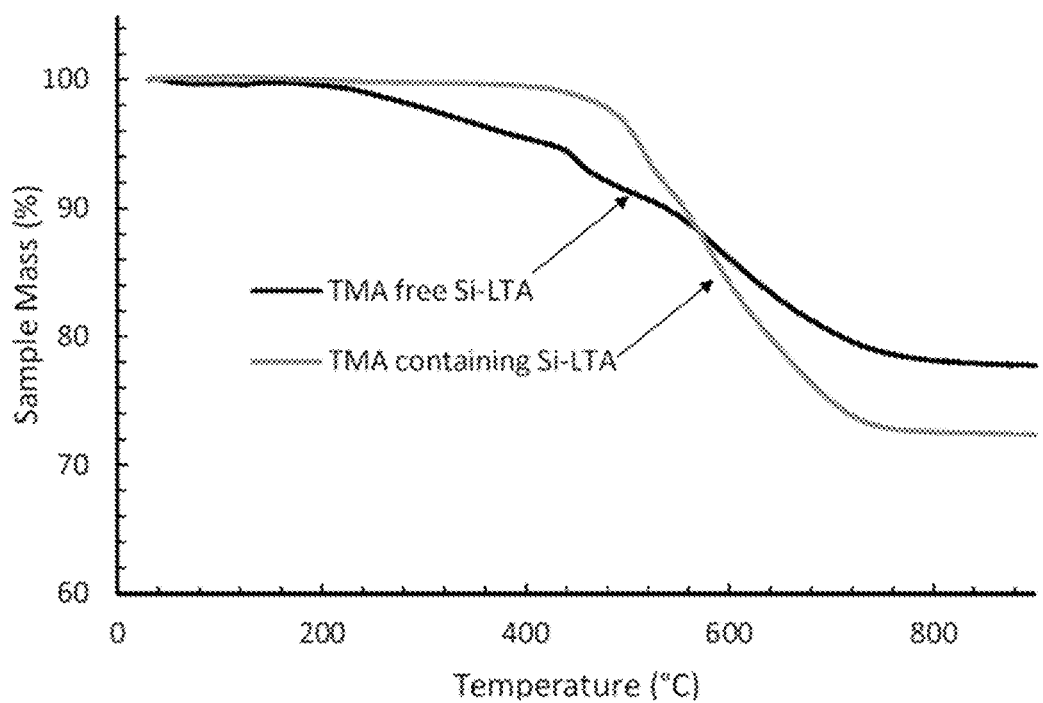
FIG. 10 shows a TGA analysis of as-made pure-silica LTA made with and without TMA.

The role of the OSDA was also studied computationally. TGA analysis FIG. 10 shows that two molecules are occluded per unit cell of LTA. This knowledge and the fact that the OSDA is too large to fit in the small sodalite cage means that two molecules of OSDA are occluded in each α-cage. Molecular dynamics calculations showed that the stabilization energy (i.e., the difference in energy of the zeolite with occluded OSDAs and the isolated zeolite and OSDAs) was an advantageous −16.9 kJ/(mol Si). The molecular modelling agreed well with the occupancy determined by TGA as the stabilization energy was only −7.36 kJ/(mol Si) if a single OSDA is occluded per cage. For methylated julolidine a maximum stabilization energy of −14.27 kJ/(mol Si) and an average stabilization energy of −13.03 kJ/(mol Si) were found. The molecular modelling showed that the conformation of the methyl groups was most likely different than has been previously reported since the most stable conformation in the α-cage was with the methyl groups pointing away from the dimerization complex, not towards the complex as was assumed based upon the single crystal structure of the pure organic. The molecular modelling also agreed with previous studies that found AST as the product if the methylated julolidine did not dimerize properly as the stabilization energy for a single OSDA per cage is only −6.35 kJ/(mol Si), reinforcing the idea that the dimerization of the OSDA to form a supramolecular complex is key to the formation of LTA. The molecular modelling showed how this relatively simple OSDA was able to fill such a large cavity, in a similar manner to the supramolecular assembly formed from methylated julolidine.

Example 4.5. Single Crystal X-Ray Crystallography

The as-made materials (with and without TMA in the synthesis) as well as the calcined material were studied using single crystal X-ray diffraction. The unit cell parameters are shown for each of the samples in Tables 3, 4, and 5, respectively. In the as-made material containing TMA, the structure analysis confirmed that TMA was present in the sodalite cages (though not all are occupied) and that the carbon atoms were completely disordered. The cages were symmetrical, so there was no reason that long range order with respect to the LTA structure should be expected. It was also found that the fluoride location could be resolved to the D4Rs in both as-made materials; the preferential location of fluoride in D4Rs has been often reported and is normally given as one reason that fluoride-mediated syntheses lead to many structures containing D4Rs.

Even lowering the symmetry of the structure did not help to resolve the location of the disordered OSDAs. As the large α-cage of LTA is very symmetrical, it was unlikely that the organic material would adopt any symmetrical, long range conformation so this result was also expected, but meant that the single crystal analysis could not be used to confirm the results of the molecular modelling study.

TABLE 3

Unit cell data at −173° C. for Sample No. P15133
(as-made, no TMA used in pure-silica LTA synthesis).

| Crystal system | | | Cubic | | |
|---|---|---|---|---|---|
| Space group | Pm-3m | a | 11.813(3) Å | α | 90° |
| | | b | 11.813(3) Å | β | 90° |
| | | c | 11.813(3) Å | γ | 90° |
| V | 1648.5(13) Å3 | | | | |
| Z | 24 | | | | |
| Dc | 1.491 g · cm$^{-1}$ | | | | |

TABLE 4

Unit cell data at −173° C. for Sample No. P15134
(as-made, TMA used in pure-silica LTA synthesis)

| Crystal system | | | Cubic | | |
|---|---|---|---|---|---|
| Space group | Pm-3m | a | 11.824(5) Å | α | 90° |
| | | b | 11.824(5) Å | β | 90° |
| | | c | 11.824(5) Å | γ | 90° |
| V | 1653(2) Å3 | | | | |
| Z | 24 | | | | |
| Dc | 1.57 g · cm–1 | | | | |

TABLE 5

Unit cell data at −173° C. for Sample
No. P15133 (Calcined pure-silica LTA)

| Crystal system | | | Cubic | | |
|---|---|---|---|---|---|
| Space group | Pm-3m | a | 11.857(4) Å | α | 90° |
| | | b | 11.857(4) Å | β | 90° |
| | | c | 11.857(4) Å | γ | 90° |
| V | 1667.0(17) Å3 | | | | |
| Z | 24 | | | | |
| Dc | 1.437 g · cm$^{-1}$ | | | | |

Example 4.2

Crystalline Aluminosilicate Material where Si:Al=30.8.

Example 4.2.1

Figure 11:
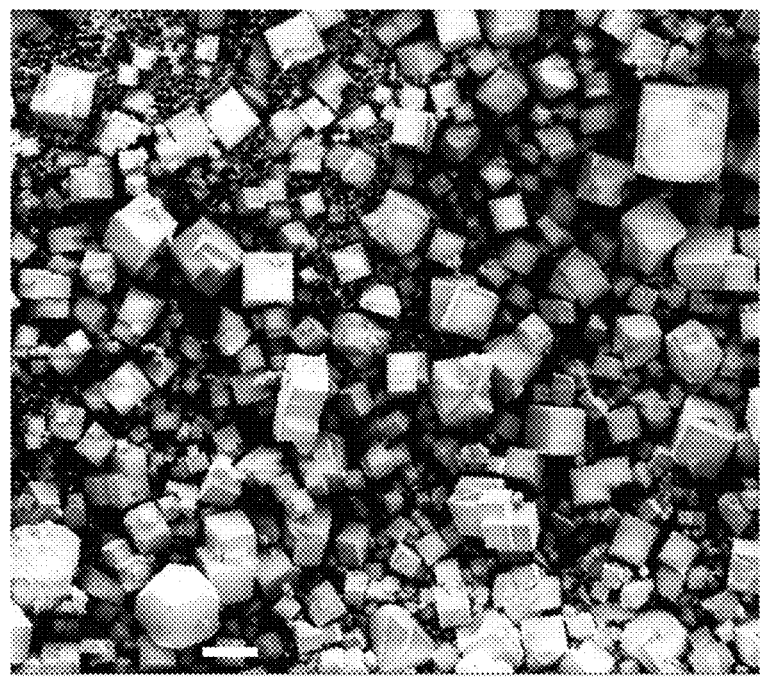
FIG. 11 shows an SEM image of aluminosilicate LTA produced in fluoride mediated reactions. Bar=30 microns.

Scanning Electron Microscopy (SEM) and: As described above, the morphology of one of the aluminosilicate materials was studied using scanning electron microscopy (SEM) and the Si/Al ratio of the crystalline products was determined using energy-dispersive X-ray spectroscopy (EDS). SEM images can be found in FIG. 11. The average molar ratio of Si:Al for the material with gel having a molar ratio of Si:Al of 50 was found to be 30.8.

Example 4.2.2

A representative powder X-ray diffraction pattern (PXRD) of one of the aluminosilicate LTA materials obtained is shown in FIG. 12 along with the calcined material. All peaks match the reported spectra for LTA.

Example 4.2.3

Figure 13B:
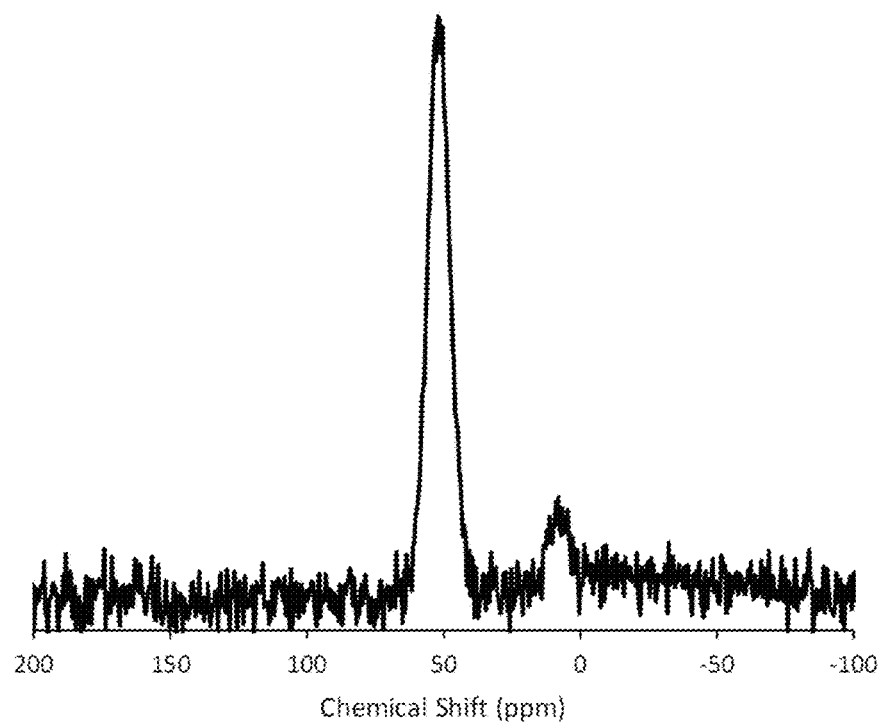
Figure 13C:
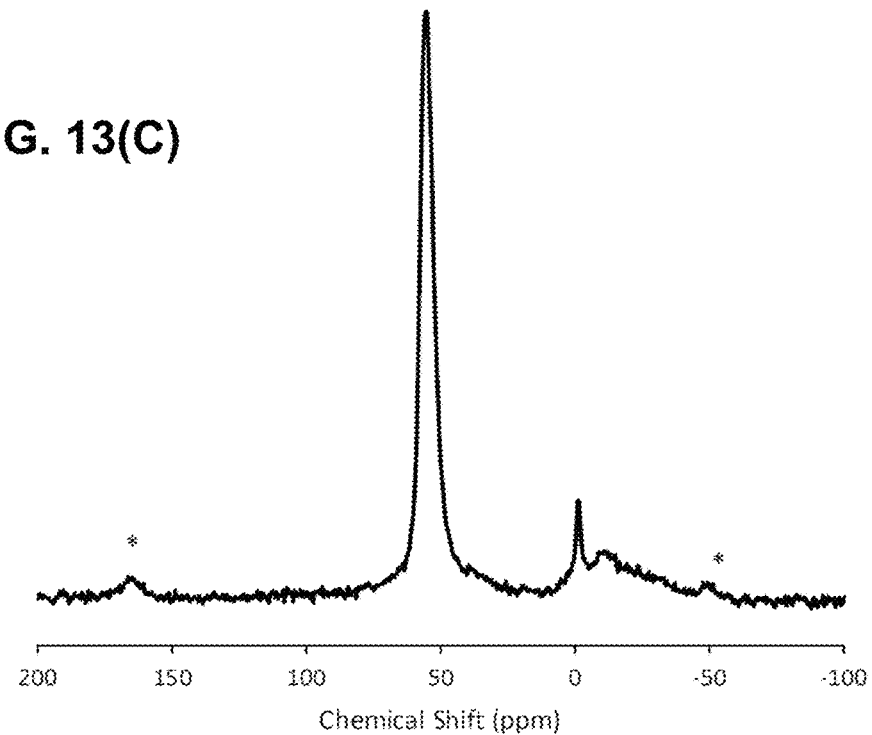

The aluminosilicate material was further characterized by solid state NMR. Solid state $^{27}$Al NMR of one of the aluminosilicate LTA samples showed that all of the aluminum was in a tetrahedral coordination environment (FIG. 13). Samples of aluminosilicate LTA were synthesized in fluoride media over a wide product compositional range (product Si/Al=12-42, see Table 1). The sample used as the source of the NMR in FIG. 13(C) was a calcined sample containing the largest amount of aluminum (Si/Al=12). Even in this case, the $^{27}$Al MAS NMR spectrum showed that nearly all of the aluminum was tetrahedral and therefore incorporated in the framework.

Example 4.3

Germanosilicate and Titanosilicate Materials

Representative powder X-ray diffraction pattern (PXRD) of two of the germanosilicate LTA materials obtained from different gel compositions are shown in FIG. 14. All peaks match the reported spectra for LTA.

Figure 15:
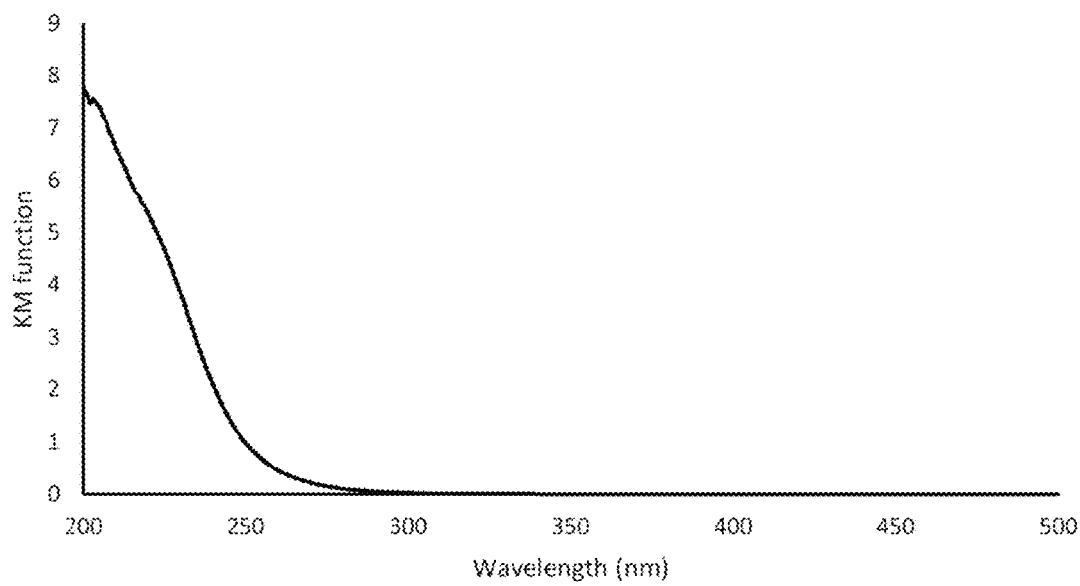
FIG. 15 shows a DR-UV spectrum of titanosilicate LTA

Lewis acidic LTA was prepared by the addition of titanium as a heteroatom. The incorporation of titanium was studied through Diffuse Reflectance (DR)-UV spectroscopy (FIG. 15), showing tetrahedral (framework) titanium. This material may have possible applications in low temperature oxidations of small molecules where the 8 MR ring and large, spherical cage size and may show advantages over larger pore materials such as TS-1 and Ti-BEA. Ti-LTA was shown to be catalytically active for epoxidation reactions by using it as a catalyst for the epoxidation of allyl alcohol with $H_2O_2$.

Example 5. MTO Reactivity

Example 3.1. Methods

Prior to reaction testing, samples were calcined in breathing-grade air by initially holding them at 150° C. for 3 h (at a heating rate of 1° C./min) before heating the samples further to 580° C. for 6 h (again at a 1° C./min heating rate) to convert them to their proton forms. Calcined samples were then pelletized, crushed, and sieved. Particles between 0.6 and 0.18 mm were supported between glass wool beds in an Autoclave Engineers BTRS, Jr. SS-316 tubular, continuous flow reactor. All catalysts were dried at 150° C. in situ in a 30 cm$^3$/min flow of 5% Ar/95% He for 4 h prior to the reaction. The reactions were conducted at 400° C. in a 10% methanol/inert flow. Methanol was introduced via a liquid syringe pump at 5.4 μL/min into a gas stream of the inert blend at 30 cm3/min. The reactant flow had a weight hourly space velocity of 1.3 h$^{-1}$. In a typical run, 200 mg of dry catalyst was loaded. Effluent gases were evaluated using an on-stream GC/MS (Agilent GC 6890/MSD5793N) with a Plot-Q capillary column installed. Conversions and selectivities were computed on a carbon mole basis.

Example 5.2

Figure 16:
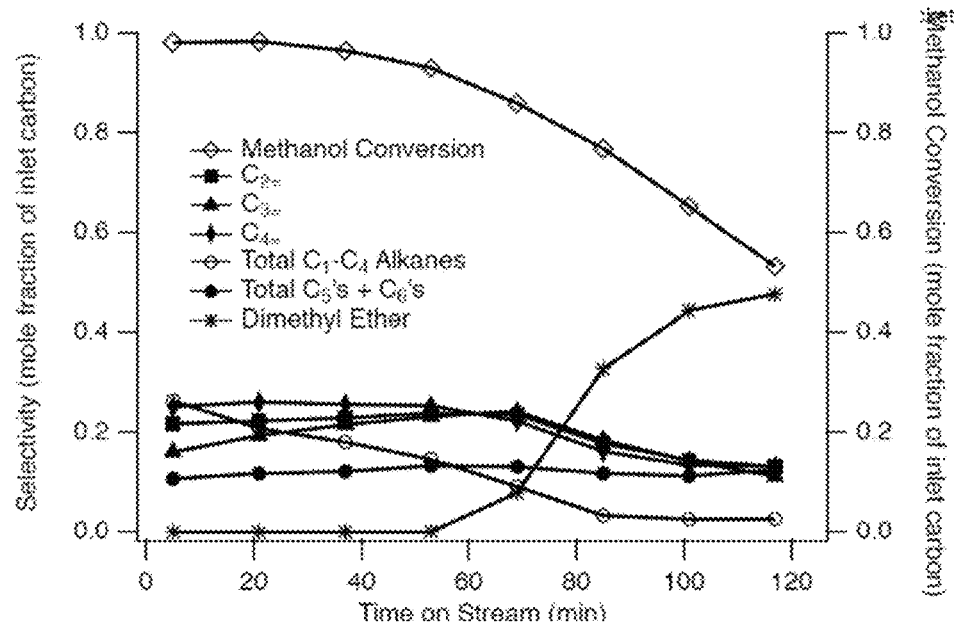
FIG. 16 shows MTO reaction data for calcined aluminosilicate LTA.
Figure 17A:
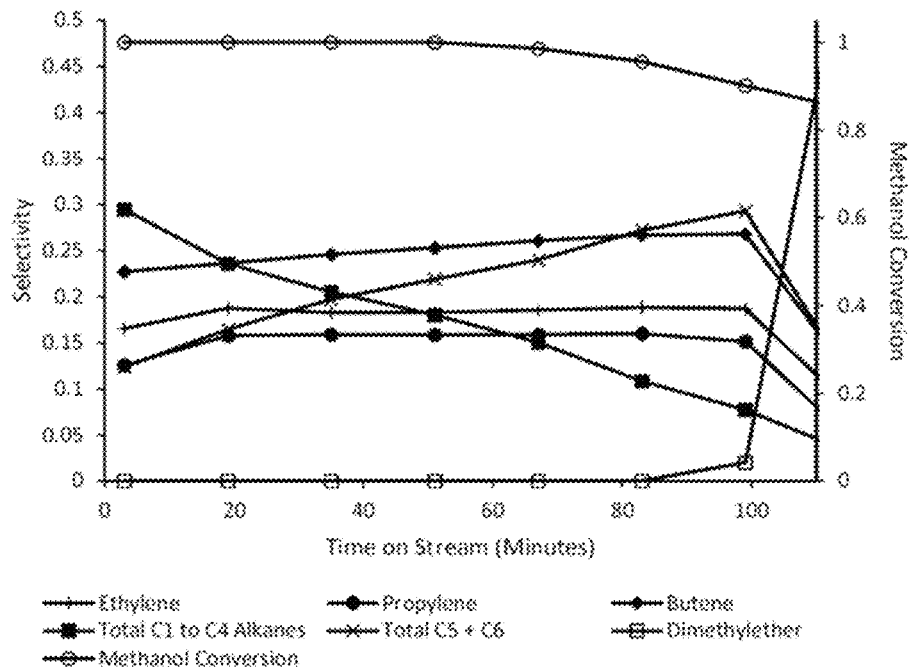
FIGS. 17(A-D) show MTO reaction data for calcined aluminosilicate LTA, in samples where Si/Al=12 (FIG. 17(A)); Si/Al=33 (FIG. 17(B)); Si/Al=38 (FIG. 1T(C)); and Si/Al=42 (FIG. 17(D)).
Figure 17B:
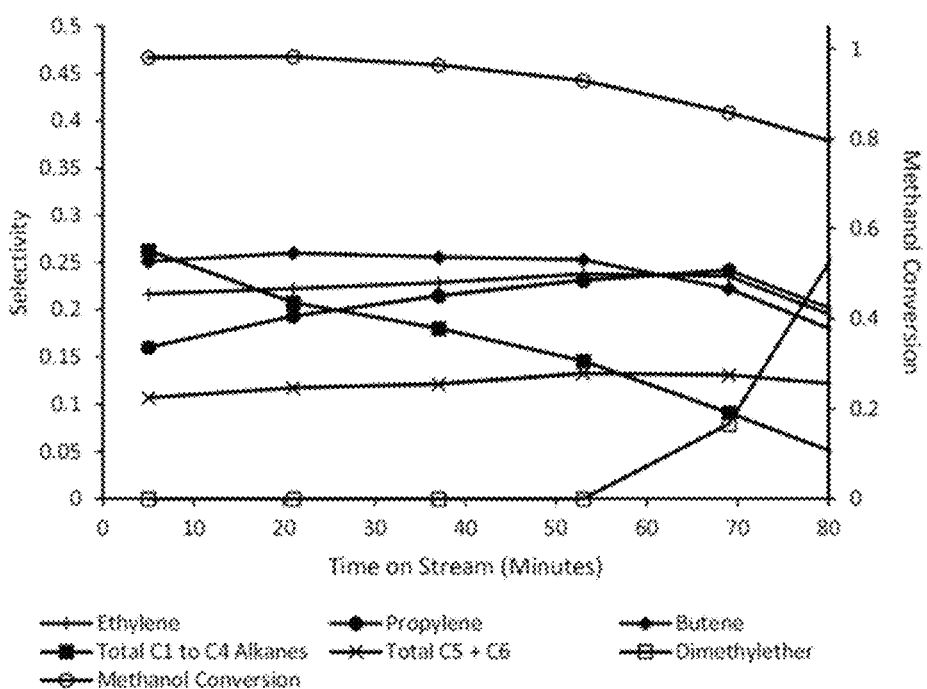
Figure 17C:
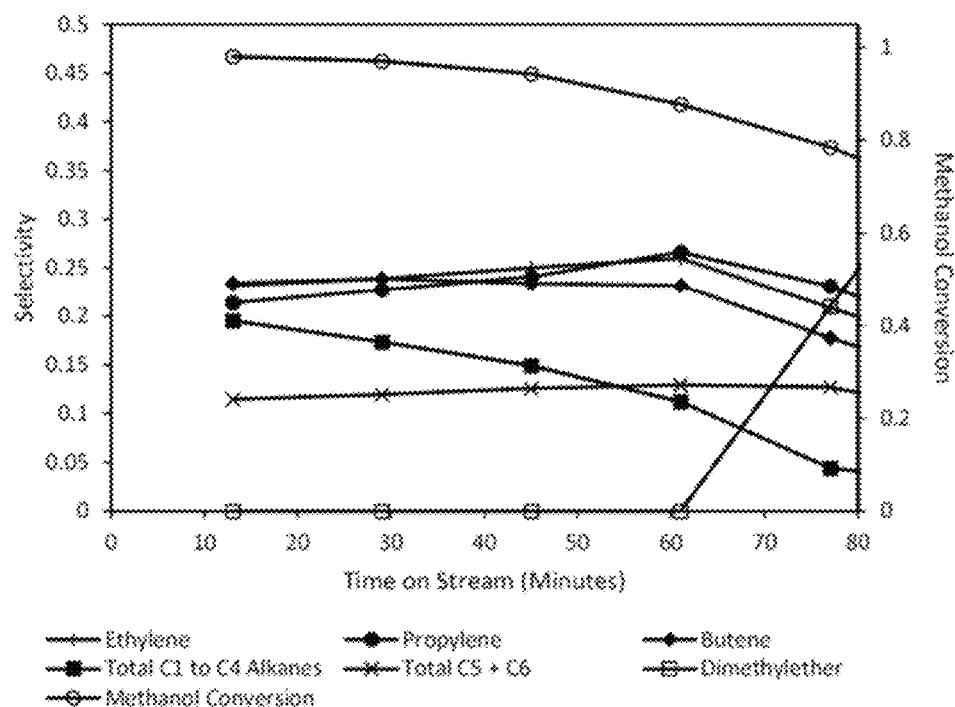
Figure 17D:
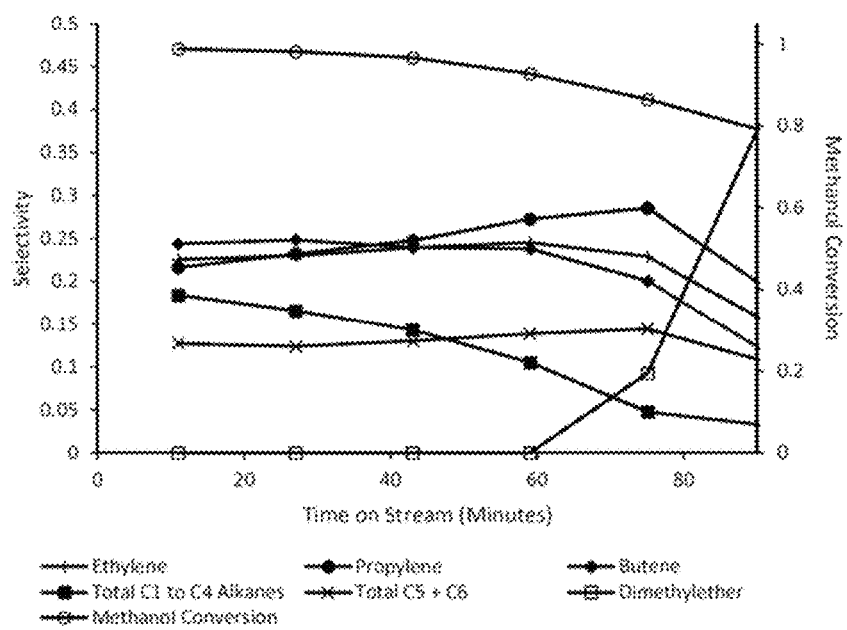
Figure 18A:
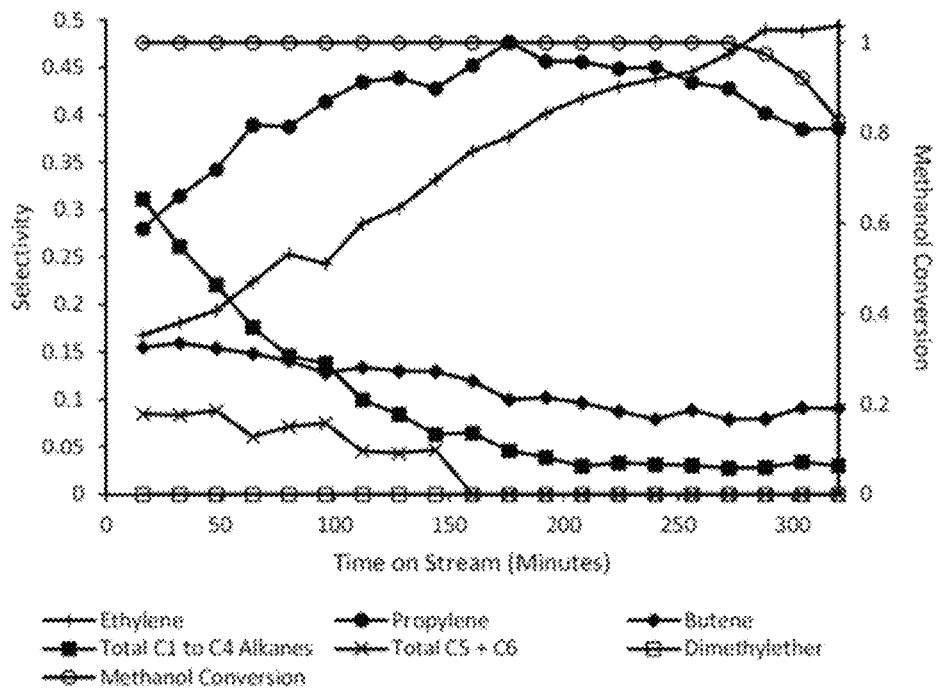
FIGS. 18(A-D) show MTO reaction data for samples of structure SSZ-13 (Si/Al=19) (FIG. 18(A)); SAPO-34 (FIG. 18(B)); RTH (Si/Al=17) (FIG. 18(C)); and RTH (Si/Al=29) (FIG. 18(D)).
Figure 18B:
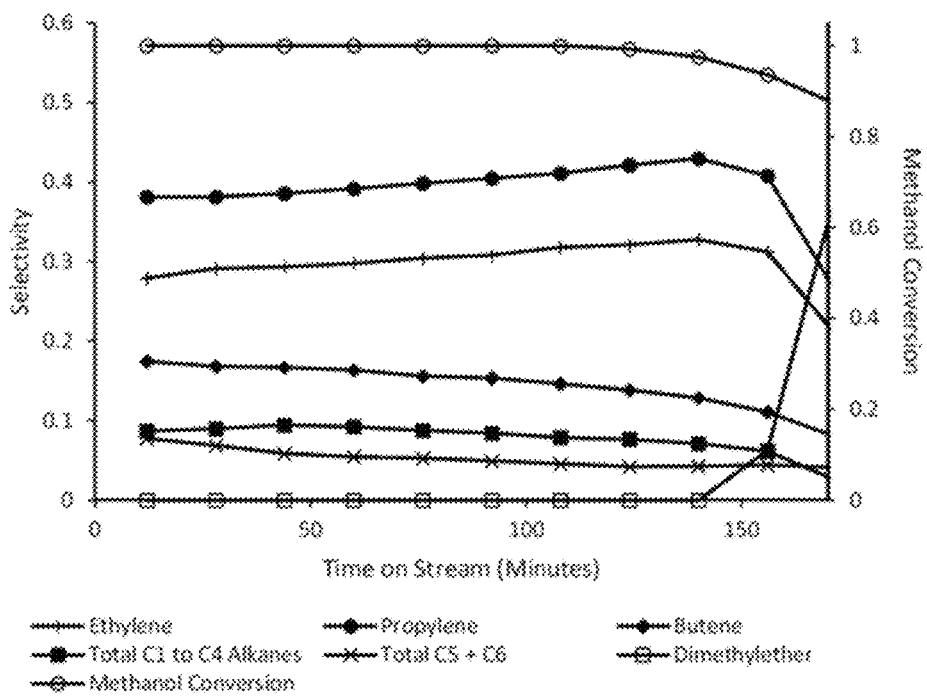
Figure 18C:
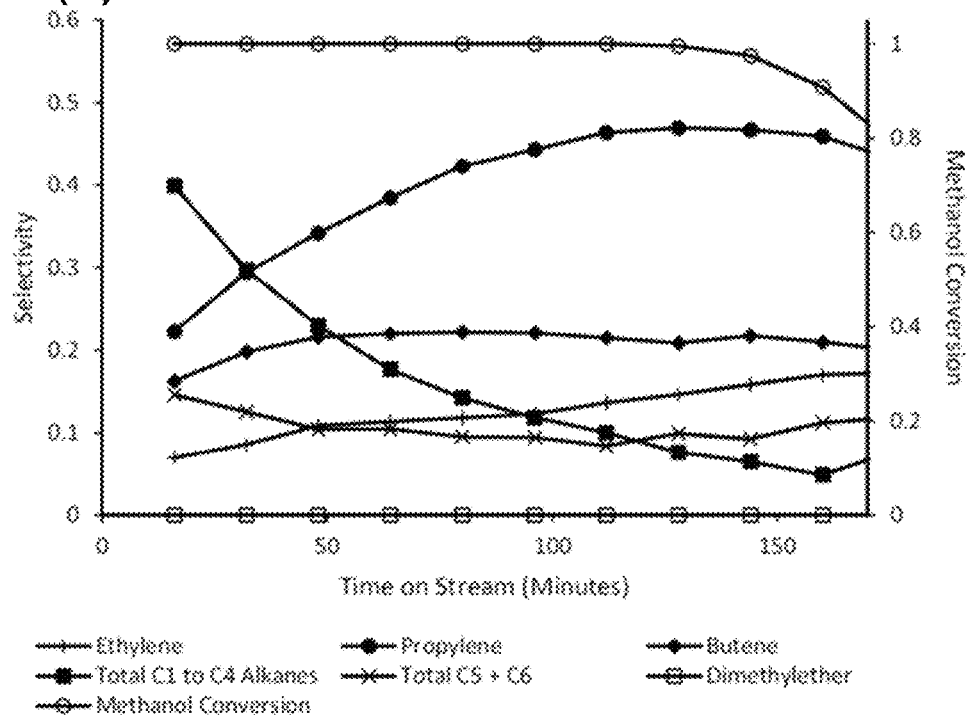
Figure 18D:
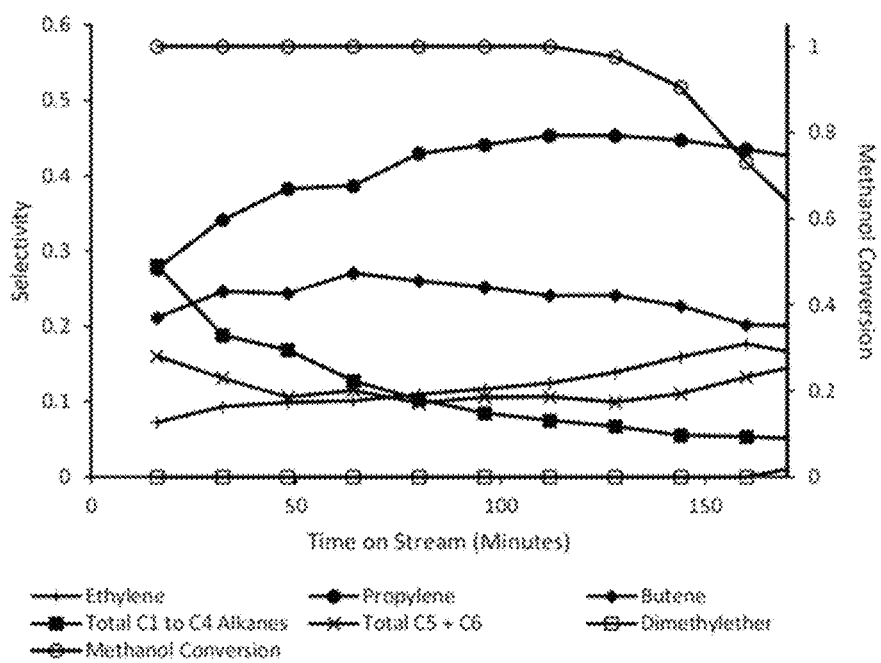

Preliminary time-on-stream (TOS) reaction data are shown for the calcined aluminosilicate LTA in FIG. 16. The calcined LTA (Si/Al=30.8), while initially active in producing $C_2$-$C_4$ olefins, also produces a large amount of $C_1$-$C_4$ alkanes. This sample deactivated rapidly (approximately 70 min TOS), accompanied by drops in olefin selectivities and a simultaneous rise in dimethyl ether (DME) production.

Example 5.3

A more expanded investigation into the MTO reaction involved the use of four different samples of LTA with product Si/Al=12, 33, 38, 42. The results are compared to SSZ-13, SAPO-34 and aluminosilicate RTH (see below). The time dependent reaction profiles for each the materials are different and data are listed in Table 6 for comparison at around 50 minutes. Additional data are provided for SSZ-13, SAPO-34 and RTH that had longer lifetimes than the LTAs. The respective profiles are shown in FIGS. 17(A-D) and FIGS. 18(A-D).

Some interesting comparisons can be made between the various frameworks. SSZ-13 and SAPO-34 show the highest maximum olefin selectivity, and have a high selectivity to ethylene and propylene. RTH gives a lower selectively to ethylene, but higher selectivity to butenes as well as $C_5$ and $C_6$ products. Aluminosilicate LTA shows a relatively low selectively to ethylene and propylene, but produces the highest selectively to butenes as well as $C_5$ and $C_6$ products. Both the reaction selectivities and faster deactivation times appear to be related to the larger cage.

TABLE 6

MTO reaction results at maximum C2 to C4 olefin selectivity. Full reaction profiles for each material can be found in FIGS. 17(A-D) and FIGS. 18(A-D). TOS is Time on Stream. SSZ-13, SAPO-34, and RTH samples were prepared according to the methods of J. E. Schmidt, M. A. Deimund, M. E. Davis, Chem. Mater. 2014, 26, 7099-7105

| | | | | Selectivities | | | | | |
|---|---|---|---|---|---|---|---|---|---|
| Material | Si/Al | TOS (min) | Methanol conversion | $C_2$-$C_4$ Olefins | Ethylene | Propylene | Butenes[a] | $C_1$-$C_4$ Unsaturates[b] | $C_5 + C_6$[c] |
| LTA | 12 | 51 | 7 | 0.60 | 0.18 | 0.16 | 0.25 | 0.18 | 0.22 |
| LTA | 33 | 53 | 0.93 | 0.72 | 0.24 | 0.24 | 0.25 | 0.15 | 0.13 |
| LTA | 38 | 45 | 0.94 | 0.72 | 0.24 | 0.25 | 0.23 | 0.15 | 0.13 |
| LTA | 42 | 43 | 0.97 | 0.73 | 0.24 | 0.24 | 0.24 | 0.15 | 0.13 |
| SSZ-13 | 19 | 48 | 1.00 | 0.69 | 0.19 | 0.19 | 0.15 | 0.22 | 0.09 |
| | 19 | 208 | 1.00 | 0.97 | 0.42 | 0.42 | 0.10 | 0.003 | 0.00 |
| SAPO-34 | — | 44 | 1.00 | 0.85 | 0.29 | 0.29 | 0.17 | 0.09 | 0.06 |
| | — | 108 | 1.00 | 0.88 | 0.32 | 0.32 | 0.15 | 0.08 | 0.05 |
| RTH | 17 | 48 | 1.00 | 0.67 | 0.11 | 0.11 | 0.22 | 0.23 | 0.10 |
| | 17 | 128 | 1.00 | 0.82 | 0.15 | 0.15 | 0.21 | 0.08 | 0.10 |
| RTH | 29 | 48 | 1.00 | 0.73 | 0.10 | 0.10 | 0.24 | 0.17 | 0.11 |
| | 29 | 112 | 1.00 | 0.82 | 0.12 | 0.12 | 0.24 | 0.07 | 0.11 |

[a]Butenes include all isomeric butenes (but-1-ene, (Z)-but-2-ene, (E)-but-2-ene and 2-methylpropene
[b]Selectivity to all fully saturated hydrocarbons containing 1 to 4 carbon atoms
[c]Selectivity to all 5 and 6 carbon species T Geometrical properties of the three frameworks tested for the MTO reaction are given in Table 7.

TABLE 7

Geometrical Properties of Frameworks Tested for MTO Reactions[a]

| Framework | Channel system | 8MR opening (Å) | $D_M$ (Å)[b] | $D_a$ (Å)[c] | $D_b$ (Å)[c] | $D_c$ (Å)[c] |
|---|---|---|---|---|---|---|
| CHA | 3D | 3.8 × 3.8 | 7.37 | 3.72 | 3.72 | 3.72 |
| LTA | 3D | 4.1 × 4.1 | 11.05 | 4.21 | 4.2 | |
| RTH | 3D | 3.8 × 3.8<br>2.5 × 5.6 | 8.18 | 4.14 | 1.67 | 2.67 |

[a]All data obtained from the IZA Web site.
[b]$D_M$ is the maximum included sphere diameter within cages of the material.
[c]$D_a$, $D_b$, and $D_c$ are the maximum free sphere diameters that can diffuse along the a, b, and c axes, respectively.

Example 6. Epoxidation Reaction Testing

Allyl alcohol (1.0 mmol), $H_2O_2$ (1 equivalent, provided using in a 30% solution, and an Ti-LTA catalyst (50 mg) were stirred in 5 mL of methanol solvent for 24 hours at 55° C. The solution was then centrifuged to remove the solid catalyst. The remaining liquid was rotor-evaporated to remove the solvent, leaving a clear oil, which was shown to be a mixture of starting material and epoxide by $^1$H NMR. The ratio of product epoxide:allyl alcohol was found to be 1:2.

The following references may be useful in understanding certain aspects of the present disclosure:

(1) Breck, D. W.; Eversole, W. G.; Milton, R. M.; Reed, T. B.; Thomas, T. L. J. Am. Chem. Soc. 1956, 78, 5963-5972.
(2) Corma, A.; Rey, F.; Rius, J.; Sabater, M. J.; Valencia, S. Nature 2004, 431 287-290.
(3) Huang, A.; Weidenthaler, C.; Caro, J. Microporous Mesoporous Mater. 2010, 130, 352-356.
(4) C. Baerlocher, L. B. Mccusker, "Database of Zeolite Structures, <http://www.iza-structure.org/databases/>. Accessed Dec. 8, 2014.," 2014.
(5) B. Yilmaz, U. Müller, Top. Catal. 2009, 52, 888-895.
(6) S. I. Zones, Microporous Mesoporous Mater. 2011, 144, 1-8.
(7) R. Pophale, F. Daeyaert, M. W. Deem, J. Mater. Chem. A 2013, 1, 6750-6760.
(8) M. Moliner, C. Martinez, A. Corma, Chem. Mater. 2014, 26, 246-258.
(9) W. Vermeiren, J.-P. Gilson, Top. Catal. 2009, 52, 1131-1161.
(10) G. Lewis, M. Miller, J. Moscoso, Stud. Surf Sci. Catal. 2004, 154, 364-372.
(11) J. W. Park, J. Y. Lee, K. S. Kim, S. B. Hong, G. Seo, Appl. Catal. A Gen. 2008, 339, 36-44.
(12) A. Huang, J. Caro, Chem. Commun. (Camb). 2010, 46, 7748-50
(13) I. Tiscornia, S. Valencia, A. Corma, C. Téllez, J. Coronas, J. Santamaría, Microporous Mesoporous Mater. 2008, 110, 303-309.
(14) H. K. Hunt, C. M. Lew, M. Sun, Y. Yan, M. E. Davis, Microporous Mesoporous Mater. 2010, 130, 49-55.
(15) M. Sun, H. K. Hunt, C. M. Lew, R. Cai, Y. Liu, Y. Yan, Chinese J. Catal. 2012, 33, 85-91.
(16) B. Harbuzaru, J.-L. Paillaud, J. Patarin, N. Bats, L. Simon, C. Laroche, U.S. Pat. No. 7,056,490 2006.
(17) J. E. Schmidt, S. I. Zones, D. Xie, M. E. Davis, Microporous Mesoporous Mater. 2014, 200, 132-139.
(18) E. J. Fayad, N. Bats, C. E. a Kirschhock, B. Rebours, A.-A. Quoineaud, J. a Martens, Angew. Chem. Int. Ed. Engl. 2010, 49, 4585-8.
(19) S. I. Zones, R. J. Darton, R. Morris, S.-J. Hwang, J. Phys. Chem. B 2005, 109, 652-61.
(20) J. E. Schmidt, M. A. Deimund, M. E. Davis, Chem. Mater. 2014, 26, 7099-7105.
(21) Pophale, R.; Daeyaert, F.; Deem, M. W. Computational Prediction of Chemically Synthesizable Organic Structure Directing Agents for Zeolites. J. Mater. Chem. A 2013, 1 (23), 6750-6760.
(22) Corma, A.; Rey, F.; Rius, J.; Sabater, M. J.; Valencia, S. Supramolecular Self-Assembled Molecules as Organic Directing Agent for Synthesis of Zeolites. Nature 2004, 431 (7006), 287-290.
(23) J. E. Schmidt and M. E. Davis, WO2014210560

As those skilled in the art will appreciate, numerous modifications and variations of the present invention are possible in light of these teachings, and all such are contemplated hereby. For example, in addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

All of the references cited in this disclosure are incorporated by reference herein in their entireties for all purposes.

What is claimed:
1. A calcined crystalline microporous silicate of LTA topology that is an aluminosilicate having a molar ratio of Si:Al in a range of from about 12 to about 42 and containing no germanium oxide or a titanosilicate; wherein
the calcined crystalline microporous silicate of LTA topology is derived from or derivable from:
(a) hydrothermally treating an aqueous composition comprising:
(i) a source of a silicon oxide;
(ii) an optional source of aluminum oxide;
(iii) an optional source of titanium oxide;
(iv) an optional source of one or more of boron oxide, gallium oxide, hafnium oxide, iron oxide, tin oxide, titanium oxide, indium oxide, vanadium oxide, zinc oxide, zirconium oxide, or combination or mixture thereof;
(v) a mineralizing agent; and
(vi) an organic structure directing agent (OSDA) comprising a substituted benzyl-3H-imidazol-1-ium cation of Formula (I):

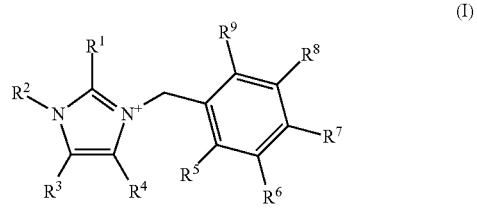

under conditions effective to crystallize an as-formed crystalline microporous silicate of LTA topology;

wherein
R$^1$, R$^2$, and R$^7$ are independently C$_{1-3}$ alkyl;
R$^3$, R$^4$, R$^5$, R$^6$, R$^8$, and R$^9$ are independently H or C$_{1-3}$ alkyl;
(b) isolating the as-formed crystalline microporous silicate of LTA topology; and
(c) calcining the as-formed crystalline microporous silicate of LTA topology to form the calcined calcined aluminosilicate having a molar ratio of Si : Al in a range of from about 12 to about 42 and containing no germanium oxide or the titanosilicate.

2. The calcined crystalline microporous silicate of LTA topology of claim 1, wherein the organic structure directing agent comprises the structure:

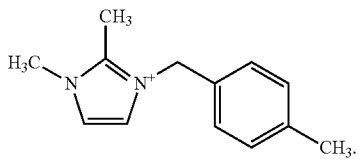

3. The calcined crystalline microporous silicate of claim 1, that is the aluminosilicate having a molar ratio of Si : Al in a range of from about 33 to about 42 and containing no germanium oxide.

4. The calcined crystalline microporous silicate of claim 1, that is the aluminosilicate having a molar ratio of Si : Al in a range of from about 12 to about 42 and containing no germanium oxide.

5. A calcined crystalline microporous titanosilicate of LTA topology; wherein
the calcined crystalline microporous titanosilicate of LTA topology is derived from or derivable from:
(a) hydrothermally treating an aqueous composition comprising:
(i) a source of a silicon oxide;
(ii) a source of titanium oxide;
(iii) an optional source of one or more of aluminum oxide, boron oxide, gallium oxide, germanium oxide, hafnium oxide, iron oxide, tin oxide, titanium oxide, indium oxide, vanadium oxide, zinc oxide, zirconium oxide, or combination or mixture thereof;
(vi) a mineralizing agent and
(vii) an organic structure directing agent (OSDA) comprising a substituted benzyl-3H-imidazol-1-ium cation of Formula (I):

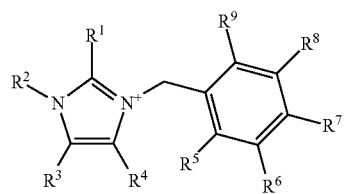

(I)

under conditions effective to crystallize an as-formed crystalline microporous silicate of LTA topology;
wherein
R$^1$, R$^2$, and R$^7$ are independently C$_{1-3}$ alkyl;
R$^3$, R$^4$, R$^5$, R$^6$, R$^8$, and R$^9$ are independently H or C$_{1-3}$ alkyl;

(b) isolating the as-formed crystalline microporous titanosilicate of LTA topology; and
(c) calcining the as-formed crystalline microporous titanosilicate of LTA topology to form the calcined titanosilicate.

6. The calcined crystalline microporous silicate of claim 4, wherein the aluminosilicate is a pure aluminosilicate.

7. The calcined crystalline microporous aluminosilicate of claim 4, comprising pores containing Li, Na, K, Rb, Cs, Be, Mg, Ca, Sr, Be, Al, Ga, In, Zn, Ag, Cd, Ru, Rh, Pd, Pt, Au, Hg, La, Ce, Pr, Nd, Pm, Sm, Eu, or R$_{4-n}$N$^+$H$_n$ cations, where R is alkyl, and n=0-4.

8. The calcined crystalline microporous aluminosilicate of claim 4, comprising pores containing scandium, yttrium, titanium, zirconium, vanadium, manganese, chromium, molybdenum, tungsten, iron, ruthenium, osmium, cobalt, rhodium, iridium, nickel, palladium, platinum, copper, silver, gold, or a mixture thereof, each as a metal, oxide, or salt.

9. The calcined crystalline microporous aluminosilicate of claim 4, comprising pores containing copper as a metal, oxide, or salt.

10. The calcined crystalline microporous aluminosilicate of claim 4, exhibiting a powder XRD pattern having at least five peaks selected from the group consisting of 7.3°±0.3° 2-theta; 10.4°±0.3° 2-theta; 12.8°±0.3° 2-theta; 16.6°±0.3° 2-theta; 21.1°±0.3° 2-theta; 22.4°±0.3° 2-theta; and 24.7°±0.3° 2-theta.

11. The calcined crystalline microporous aluminosilicate of claim 4, further exhibiting at least one of:
(a) an XRD diffraction pattern as those shown in FIG. 12; and/or
(b) an $^{27}$Al MAS spectrum as shown in FIG. 13(A) or (B).

12. A process for catalyzing a reaction using a crystalline microporous silicate of claim 4, the process comprising (a) carbonylating dimethyl ether (DME) with CO at low temperatures, (b) reducing NOx with methane, (c) cracking or hydrocracking a hydrocarbon, (d) dehydrogenating, (e) converting paraffins to aromatics, (f) converting methanol to olefins, (g) isomerizing xylenes, (h) disproportionating toluene, (i) alkylating aromatic hydrocarbons, (j) oligomerizing alkenes, (k) aminating lower alcohols, (1) separating and sorbing lower alkanes, (m) dewaxing a hydrocarbon feedstock, (n) isomerizing an olefin, (o) producing a higher molecular weight hydrocarbon from lower molecular weight hydrocarbon, (p) reforming a hydrocarbon, converting a lower alcohol or other oxygenated hydrocarbon to produce an olefin products, (q) epoxiding olefins with hydrogen peroxide, (r) reducing the content of an oxide of nitrogen contained in a gas stream in the presence of oxygen, or (s) separating nitrogen from a nitrogen-containing gas mixture by contacting the respective feedstock with the a catalyst comprising the calcined crystalline microporous aluminosilicate of claim 2 under conditions sufficient to affect the named transformation.

13. The process of claim 12, comprising reducing NO$_x$ with methane, the method comprising contacting a mixture containing NO$_x$ and methane with a catalyst comprising the calcined crystalline microporous aluminosilicate of claim 2 under conditions sufficient to reduce the NOx content of the mixture.

14. A process for converting a lower alcohol or other oxygenated hydrocarbon to produce an olefin product, the process comprising contacting the lower alcohol or other oxygenated hydrocar with a catalyst comprising the calcined crystalline microporous aluminosilicate of claim 4 under conditions sufficient to produce the olefin product.

15. The process of claim 14, wherein the lower alcohol or other oxygenated hydrocarbon is methanol.

16. The calcined crystalline microporous aluminosilicate of LTA topology of claim 4 that is derived or derivable from:
(a) hydrothermally treating an aqueous composition comprising:
   (i) a source of a silicon oxide;
   (ii) a source of aluminum oxide; and
   (iii) an organic structure directing agent (OSDA) comprising the structure:

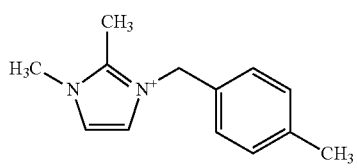

(I)

under conditions effective to crystallize an as-formed crystalline microporous aluminosilicate of LTA topology;
(b) isolating the as-formed crystalline microporous aluminosilicate of LTA topology; and
(c) calcining the as-formed crystalline microporous aluminosilicate of LTA topology to form the calcined aluminosilicate having a molar ratio of Si : Al in a range of from about 12 to about 42 and containing no germanium oxide.

17. A calcined crystalline microporous aluminosilicate of LTA topology having a molar ratio of Si : Al in a range of from about 5 to about 50 and comprising pores containing NaCl or KCl; wherein
the calcined crystalline microporous silicate of LTA topology is derived from or derivable from:
(a) hydrothermally treating an aqueous composition comprising:
   (i) a source of a silicon oxide;
   (ii) a source of aluminum oxide;
   (iii) an optional source of one or more of boron oxide, gallium oxide, germanium oxide, hafnium oxide, iron oxide, tin oxide, titanium oxide, indium oxide, titanium oxide, vanadium oxide, zinc oxide, zirconium oxide, or combination or mixture thereof;
   (iv) a mineralizing agent; and
   (v) an organic structure directing agent (OSDA) comprising a substituted benzyl-3H-imidazol-1-ium cation of Formula (I):

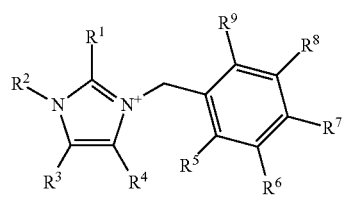

(I)

under conditions effective to crystallize an as-formed crystalline microporous silicate of LTA topology;

wherein
$R^1$, $R^2$, and $R^7$ are independently $C_{1-3}$ alkyl;
$R^3$, $R^4$, $R^5$, $R^6$, $R^8$, and $R^9$ are independently H or $C_{1-3}$ alkyl;
(b) isolating the as-formed crystalline microporous silicate of LTA topology; and
(c) calcining the as-formed crystalline microporous silicate of LTA topology to form the calcined calcined aluminosilicate having a molar ratio of Si : Al in a range of from about 5 to about 50.

18. The calcined crystalline microporous titanosilicate of LTA topology of claim 5 that is derived from or derivable from a process of:
(a) hydrothermally treating an aqueous composition comprising:
   (i) a source of a silicon oxide;
   (ii) a source of titanium oxide; and
   (iii) an organic structure directing agent (OSDA) comprising the structure:

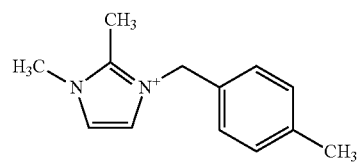

(I)

under conditions effective to crystallize an as-formed crystalline microporous titanosilicate of LTA topology;
(b) isolating the as-formed crystalline microporous titanosilicate of LTA topology; and
(c) calcining the as-formed crystalline microporous titanosilicate of LTA topology.

19. The calcined crystalline microporous titanosilicate of claim 18, comprising pores containing Li, Na, K, Rb, Cs, Be, Mg, Ca, Sr, Be, Al, Ga, In, Zn, Ag, Cd, Ru, Rh, Pd, Pt, Au, Hg, La, Ce, Pr, Nd, Pm, Sm, Eu, or $R_{4-n}N^+H_n$ cations, where R is alkyl, and n=0-4.

20. The calcined crystalline microporous titanosilicate of claim 18, comprising pores containing NaCl or KCl.

21. The calcined crystalline microporous titanosilicate of claim 18, comprising pores containing scandium, yttrium, titanium, zirconium, vanadium, manganese, chromium, molybdenum, tungsten, iron, ruthenium, osmium, cobalt, rhodium, iridium, nickel, palladium, platinum, copper, silver, gold, or a mixture thereof, each as a metal, oxide, or salt.

22. The calcined crystalline microporous titanosilicate of claim 18, comprising pores containing copper as a metal, oxide, or salt.

23. The calcined crystalline microporous titanosilicate of claim 18, exhibiting a powder XRD pattern having peaks selected from the group consisting of 7.3°±0.3° 2-theta; 10.4°±0.3° 2-theta; 12.8°±0.3° 2-theta; 16.6°±0.3° 2-theta; 21.1°±0.3° 2-theta; 22.4°±0.3° 2-theta; and 24.7°±0.3° 2-theta.

24. A process for epoxiding an olefin with hydrogen peroxide, comprising contacting the olefin with a catalyst comprising the calcined crystalline microporous titanosilicate solid of claim 18 under conditions sufficient to epoxide the olefin.

25. The process of claim 24, wherein the olefin is an allylic alcohol.

* * * * *